United States Patent
Crawford et al.

(10) Patent No.: US 6,410,264 B1
(45) Date of Patent: Jun. 25, 2002

(54) PICHIA PASTORIS GENE SEQUENCES AND METHODS FOR THEIR USE

(75) Inventors: Kenneth A. Crawford, Alameda; Robert Bishop, San Francisco, both of CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 09/127,578

(22) Filed: Jul. 31, 1998

Related U.S. Application Data

(60) Provisional application No. 60/054,783, filed on Aug. 5, 1997, and provisional application No. 60/069,560, filed on Dec. 12, 1997.

(51) Int. Cl.$^7$ ............................................. C12Q 1/68
(52) U.S. Cl. ........................... 435/69.1; 435/5; 435/6; 435/91.1; 435/172.3; 435/320.1; 935/72; 935/33
(58) Field of Search .................. 935/72, 33; 435/69.1, 435/6, 5, 91.1, 172.3, 320.1

(56) References Cited

U.S. PATENT DOCUMENTS

| | | |
|---|---|---|
| 5,215,898 A | 6/1993 | Bolen et al. |
| 5,324,639 A | 6/1994 | Brierley et al. |
| 5,324,660 A | 6/1994 | Gleeson et al. |
| 5,521,086 A | 5/1996 | Scott et al. |
| 5,602,034 A | 2/1997 | Tekamp-Olson |

FOREIGN PATENT DOCUMENTS

| | | |
|---|---|---|
| EP | 0 495 208 A2 | 7/1992 |
| WO | WO94/21802 | 9/1994 |
| WO | WO96/40776 | 12/1996 |
| WO | WO97/12044 | 4/1997 |

OTHER PUBLICATIONS

Genbank Database, Accession No. U52430, May 28, 1996, W.E. Payne and C.A. Keiser, "PpSEC13p".

Romanos, Michael A., et al., "Foreign Gene Expression in Yeast: A Review", *Yeast*, Jun. 1992, pp. 423–488, vol. 8, John Wiley & Sons Ltd.

Cregg, James M., et al., "Recent Advances in the Expression of Foreign Genes in *Pichia pastoris*", *Bio/Technology*, Aug. 1993, pp. 905–910, vol. 11.

Payne, William E., et al., "An Inducible Acid Phosphatase from the Yeast *Pichia pastoris*: Characterization of the Gene and Its Product", *Gene*, 1995, pp. 19–26, vol. 163, Elsevier Science B.V.

Sreekrishna, Koti, et al., "Strategies for Optimal Synthesis and Secretion of Heterologous Proteins in the Methylotrophic Yeast *Pichia pastoris*", *Gene*, 1997, pp. 55–62, vol. 190, Elsevier Science B.V.

Buckholz, Richard G., "Yeast Systems for the Expression of Heterologous Gene Products", *Current Opinion in Biotechnology*, 1993, pp. 538–542, vol. 4, Current Biology Ltd.

Busser, K., et al., "Heterologous Protein Expression in *Pichia pastoris*", *American Biotechnology Laboratory*, 1993, pp. 10–EOA, vol. 11, No.13, International Scientific Communications.

*Primary Examiner*—W. Gary Jones
*Assistant Examiner*—Janell E. Taylor
(74) *Attorney, Agent, or Firm*—W. Murray Spruill; Joseph H. Guth; Robert P. Blackburn

(57) ABSTRACT

Regulatory nucleotide sequences for a novel *Pichia pastoris* gene, designated PpSEC10 gene, and the nucleotide sequences and respective amino acid sequences for the secretion leader and the mature Sec10p protein components of the precursor polypeptide encoded by this novel gene are provided. These compositions are useful in methods for expression and secretion of proteins when assembled in proper reading frame, individually or in combination, within a DNA construct that further comprises a nucleotide sequence encoding a protein of interest. Vectors comprising the DNA constructs of the invention can be used to transform a yeast host cell, which can then be cultured to obtain the secreted protein of interest. Kits useful in this method and in methods of detection of the Sec10p protein using antibodies are also disclosed.

73 Claims, No Drawings

PICHIA PASTORIS GENE SEQUENCES AND METHODS FOR THEIR USE

CROSS-REFERENCE TO RELATED APPLICATIONS

This application claims the benefit of U.S. Provisional Application Ser. No. 60/054783, filed Aug. 5, 1997, and U.S. Provisional Application Ser. No. 60/069560, filed Dec. 12, 1997, the contents of which are herein incorporated by reference.

FIELD OF THE INVENTION

The present invention relates to the area of protein production, more particularly to yeast-derived regulatory regions and coding sequences for use in the production and secretion of heterologous proteins using a yeast host expression system.

BACKGROUND OF THE INVENTION

Yeast host expression systems have successfully been used for production and secretion of heterologous proteins. Expression of a protein of interest can be enhanced with use of yeast-recognized regulatory regions. Increased yield of a heterologous protein of interest is commonly achieved with the use of yeast-derived signal and secretion leader peptide sequences. The use of native yeast secretion leaders reportedly improves direction of the protein of interest through the secretory pathway of the yeast host. Modifications to secretion leaders such as with truncation, may further improve yield.

Pichia pastoris has proven to be a desirable yeast host for production and secretion of high levels of some heterologous proteins. Additional yeast-derived regulatory regions and native yeast secretion leaders for use in heterologous protein expression in this and other yeast hosts are needed.

SUMMARY OF THE INVENTION

Compositions and methods for expression of proteins, more particularly heterologous proteins, using a yeast host cell as the expression system are provided. Compositions of the invention are the nucleotide sequences for the promoter and terminator regions for a novel Pichia pastoris gene, designated PpSEC10 gene, and the nucleotide sequences and respective amino acid sequences for the secretion leader and the mature Sec10p protein components of the precursor polypeptide encoded by this novel gene.

These compositions are useful in methods for expression and secretion of proteins, particularly heterologous proteins. Vectors having at least one copy of a DNA construct comprising at least one of the PpSEC10-derived regulatory and coding nucleotide sequences in proper reading frame with a nucleotide sequence encoding a protein of interest are constructed. A yeast host cell transformed with such a vector can then be cultured and screened for secretion of the protein of interest.

A mutant Pichia pastoris strain that has a disabled PpSEC10 gene and which does not express the Sec10p protein is also provided for use in the methods of the present invention. The Sec10p protein is normally expressed and secreted into the culture medium at high levels. Use of the mutant yeast strain is advantageous for protein production purposes as purification of the desired protein from the culture medium is simplified.

The Sec10p protein is useful for identifying culture conditions under which the PpSEC10 promoter drives transcription of a coding sequence of interest. In this manner, antibodies to the Sec10p protein are provided for detection of this protein in the culture medium. Kits for use in the methods of protein production and detection of Sec10p protein are also provided.

DETAILED DESCRIPTION OF THE INVENTION

The present invention is directed to compositions and methods for expression and secretion of proteins, more particularly heterologous proteins, using a yeast host cell as the expression system. Compositions of the invention include isolated nucleotide sequences for the regulatory transcription initiation and termination regions of a novel Pichia pastoris gene, hereinafter designated the PpSEC10 gene, and the isolated nucleotide sequences and respective amino acid sequences for the secretion leader and for the mature Sec10p protein components of the precursor polypeptide encoded by this novel PpSEC10 gene. Variants and fragments of these PpSEC10-derived nucleotide and amino acid sequences are also encompassed by the present invention. By "isolated" is intended purified either partially or substantially as well as encompassing the use of the PpSEC10-derived nucleotide or amino acid sequences in uses other than their natural setting, for example in chimeric constructions, expression vectors, or transformation plasmids.

The PpSEC10-derived compositions disclosed herein are useful in methods directed to isolation of homologous nucleotide sequences and to expression and secretion of proteins, particularly heterologous proteins, using a yeast host expression system. These methods and additional uses for these compositions are disclosed in detail below.

The novel PpSEC10 gene of the present invention encodes a precursor polypeptide that comprises a secretion leader and a polypeptide sequence for the mature form of a 10 kDa yeast-secreted protein designated the Sec10p protein. This precursor polypeptide represents the initial translation product of mRNA transcribed from the PpSEC10 gene. The PpSEC10 precursor polypeptide has some structural components that are typical of secreted proteins: a secretion leader with a hydrophobic N-terminal sequence that is characteristic of the secretion signal, a mature protein sequence, and two basic amino acids that are positioned at the C-terminus of the secretion leader and which directly precede the mature protein sequence. Dibasic residues are a common cleavage recognition sequence for processing proteases such as Kex2. The predicted molecular weight of the mature form of Sec10p based on the protein amino acid sequence is 10 kDa, while the secreted protein's estimated weight based on SDS-PAGE mobility is 18 kDa, indicating Sec10p may be glycosylated.

Wild-type Pichia pastoris cells secrete high levels of the mature Sec10p protein following proteolytic processing of the precursor polypeptide to remove the secretion leader that directs movement of the mature Sec10p protein through the secretory pathway of the yeast cell. As disclosed below, manipulation of the nucleotide sequence encoding the Sec10p precursor polypeptide results in a mutant strain of Pichia pastoris that has a disabled PpSEC10 gene and which lacks expression of the Sec10p protein. This mutant strain is useful in methods for expression and secretion of heterologous proteins in a yeast host expression system.

The regulatory transcription initiation and termination nucleotide sequences for the PpSEC10 gene, the nucleotide sequences encoding the components of the precursor polypeptide and their respective amino acid sequences, and variants and fragments of these nucleotide and amino acid sequences are of particular interest for the purposes of this invention.

A plasmid designated pKC172 and containing the cloned PpSEC10 gene was deposited with the American Type Culture Collection, Rockville, Md., on Feb. 5, 1997 (accession number 98315, CMCC 4714). A plasmid ppGen2 in *E. coli* containing the cloned PpSEC10 gene (SEQ ID NO: 17) was deposited on Jun. 6, 1997 (accession number 98450, CMCC 4741). This deposit will be maintained under the terms of the Budapest Treaty. The PpSEC10 regulatory elements and coding sequences can be identified as portions of the plasmid DNA sequence set forth in SEQ ID NO: 17 as follows: the PpSEC10 promoter is set forth as nt 1180–228:7; the PpSEC10 secretion leader coding sequence is set forth as nt 2288–2443; the Sec10p mature protein coding sequences is set forth as nt 2444–2746; and the PpSEC10 transcription terminator is set forth as nt 2747–3061. These nucleotide sequences, and any amino acid sequences encoded thereby, are set forth individually in the sequence listing as SEQ ID NOS: 2–7 as identified below.

The sequence of the polynucleotides contained within the deposited materials, as well as the amino acid sequences of the polypeptides encoded thereby are incorporated herein by reference and are controlling in the event of any conflict with the written description of sequences herein.

Nucleotide sequences for the native transcription initiation region, also referred to as the promoter, and for the native transcription termination region, also referred to as the terminator, for the *Pichia pastoris* PpSEC10 gene are set forth in SEQ ID NOS: 2 and 3, respectively. By "transcription initiation and termination regions" is intended regulatory regions that flank a nucleotide coding sequence and control transcription of that coding sequence. The PpSEC10 transcription initiation region, or promoter, comprises a TATAA box (nt 1035–1039 of SEQ ID NO: 2) that directs RNA polymerase II to initiate downstream (3') RNA synthesis at the appropriate transcription initiation site for the PpSEC10 coding sequence. It is recognized that having identified the nucleotide sequence for the PpSEC10 promoter disclosed herein, it is within skill in the art to isolate and identify further regulatory elements, such as enhancers and the like, in the 5' untranslated region positioned upstream from the promoter sequence identified herein.

Amino acid sequences for the components of the PpSEC10 precursor polypeptide and the corresponding nucleotide sequences encoding these components are also disclosed herein. Thus, the amino acid sequence for the native PpSEC10 secretion leader and its corresponding nucleotide sequence are set forth in SEQ ID NOS: 4 and 5, respectively. The amino acid sequence for the native Sec10p mature protein sequence and its corresponding nucleotide sequence are set forth in SEQ ID NOS: 6 and 7, respectively.

The PpSEC10 secretion leader corresponds to the N-terminal sequence of the precursor polypeptide encoded by the PpSEC10 gene. At its N-terminus is a secretion signal, which comprises about 15 to about 30 amino acid residues and is characterized by a hydrophobic core.

The PpSEC10 secretion leader terminates in two basic amino acids ($Lys^{51}$ and $Arg^{52}$, SEQ ID NO: 4), a comnmon cleavage recognition site for yeast proteases such as Kex2.

Fragments and variants of these native PpSEC10-derived regulatory and coding nucleotide sequences and of the native amino acid sequences for the secretion leader or mature Sec10p protein are also encompassed by the present invention. By "fragment" is intended a portion of the regulatory or coding nucleotide sequence or a portion of the amino acid sequence. Fragments of a regulatory nucleotide sequence, i.e., the promoter or terminator, may retain their regulatory activity. Thus, for example, less than the entire PpSEC10 promoter sequence disclosed herein may be utilized to drive expression of an operably linked nucleotide sequence of interest, such as a nucleotide sequence encoding a heterologous protein. It is within skill in the art to determine whether such fragments decrease expression levels or alter the nature of expression, i.e., inducible or constitutive expression. Preferably at least about 200 nucleotides of a PpSEC10 promoter sequence will be used to drive expression of a coding sequence. Likewise, less than the entire PpSEC10 terminator may be utilized to terminate transcription of a coding sequence, with functional terminator fragments preferably comprising at least about 300 nucleotides. Fragments of a regulatory sequence that are useful as hybridization probes are preferably at least about 20 nucleotides in length, most preferably about 100 nucleotides in length.

With respect to coding sequences, fragments of a nucleotide sequence may encode polypeptide fragments that retain the biological activity of the native polypeptide, in this case the native PpSEC10 secretion leader or native mature Sec10p protein. Thus, a functional fragment of the PpSEC10 secretion leader directs movement of a mature protein of interest through the secretory pathway of a yeast cell. A functional fragment of the Sec10p protein binds to a Sec10p antibody as disclosed below. Fragments of a coding nucleotide sequence may range from at least about 20 nucleotides, about 24 nucleotides, about 50 nucleotides, about 100 nucleotides, and up to the entire nucleotide sequence encoding the PpSEC10 secretion leader or the mature Sec10p protein of the invention. Fragments of a coding nucleotide sequence that are useful as hybridization probes generally do not encode fragment polypeptides that retain biological activity of the native polypeptide.

Fragments of the invention include antisense nucleotide sequences used to decrease expression of the PpSEC10 gene. By "antisense sequence" is intended a DNA sequence that is in inverse orientation to the 5' to 3' normal orientation of that nucleotide sequence. When introduced into a cell, expression of the antisense sequence prevents normal expression of the corresponding nucleotide sequence that is in normal orientation. The antisense nucleotide sequence encodes an RNA transcript that is complementary to and capable of hybridizing to the endogenous mRNA produced by transcription of the DNA nucleotide sequence for the targeted gene. In this manner, production of the native protein encoded by the targeted gene is inhibited. For purposes of the present invention, antisense nucleotide sequences may be used to inhibit production of the Sec10p protein. Such antisense fragments may vary in length ranging from at least about 20 nucleotides, about 50 nucleotides, about 100 nucleotides, up to and including the entire coding sequence for the PpSEC10 gene.

By "variants" is intended substantially similar sequences. Thus, for nucleotide sequences, variants include those sequences that encode the PpSEC10 secretion leader or the mature Sec10p protein but that differ conservatively because of the degeneracy of the genetic code. These naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed, mutagenesis but which still encode the PpSEC10 secretion leader and mature Sec10p protein sequences disclosed in the present invention as discussed below. Generally, nucleotide sequence variants of the invention will have at least 70%, preferably at least 80%, more preferably about 90 to 95% or more, and most preferably about 98% or more sequence identity to the native nucleotide sequence.

With respect to the amino acid sequences for the secretion leader and the mature Sec10p protein, variants include those polypeptides that are derived from the native polypeptides by deletion (so-called truncation) or addition of one or more amino acids to the N-terminal and/or C-terminal end of the native polypeptide; deletion or addition of one or more amino acids at one or more sites in the native polypeptide; or substitution of one or more amino acids at one or more sites in the native polypeptide. Such variants may result from, for example, genetic polymorphisin or from human manipulation. Methods for such manipulations are generally known in the art.

For example, amino acid sequence variants of the polypeptide can be prepared by mutations in the cloned DNA sequence encoding the native PpSEC10 secretion leader or the mature Sec10p protein. Methods for mutagenesis and nucleotide sequence alterations are well known in the art. See, for example, Walker and Gaastra, eds. (1983) *Techniques in Molecular Biology* (MacMillan Publishing Company, New York); Kunkel (1985) *Proc. Natl. Acad. Sci. USA* 82:488–492; Kunkel et al. (1987) *Methods Enzymol.* 154:367–382; Sambrook et al. (1989) *Molecular Cloning: A Laboratory Manual* (2d ed., Cold Spring Harbor Laboratory Press, Plainview, N.Y.); U.S. Pat. No. 4,873,192; and the references cited therein; herein incorporated by reference. Guidance as to appropriate amino acid substitutions that do not affect biological activity of the secretion leader or the mature Sec10p protein may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred. Examples of conservative substitutions include, but are not limited to, Gly⇔Ala, Val⇔Ile⇔Leu, Asp⇔Glu, Lys⇔Arg, Asn⇔Gln, and Phe⇔Trp⇔Tyr.

One such amino acid sequence variant of the PpSEC10 secretion leader is set forth in SEQ ID NO: 8. The corresponding nucleotide coding sequence is set forth in SEQ ID NO: 9.In this variant, the amino acid residue at position 19 is asparagine, as opposed to alanine in the native secretion leader.

In constructing variants of the PpSEC10 secretion leader or mature Sec10p protein, modifications to the nucleotide sequences encoding the variants will be made such that variant polypeptides continue to possess the desired activity. Obviously, any mutations made in the DNA encoding a variant polypeptide must not place the sequence out of reading frame and preferably will not create complementary regions that could produce secondary mRNA structure.

Modifications to the native nucleotide sequence encoding the secretion leader or variants thereof will not interfere with the hydrophobic nature of the translated PpSEC10 secretion leader or with the ability of the secretion leader to direct movement of a protein sequence through the yeast secretory pathway and subsequent secretion of the protein from the yeast host cell.

Amino acid sequence variants of the secretion leader include those variants resulting from modification of the C-terminal proteolytic processing site. Thus, the native Lys-Arg processing site may be changed to other yeast-recognized proteolytic sites such as Arg-Arg, Pro-Arg, Ala-Arg, and Thr-Arg.

Other amino acid sequence variants of the secretion leader may be obtained with truncation of the C-terminal end of the leader. In making such truncations, the leader should retain a functional secretion signal, including its hydrophobic core. Thus, a truncated form of the PpSEC10 leader preferably comprises a minimum of about the first 35 contiguous amino acids of the N-terminal end and retains a yeast-recognized processing site at its C-terminal end.

In those instances where glycosylation of a secretion leader would facilitate movement of a mature protein through the yeast secretory pathway, glycosylation sites may be added to the PpSEC10 secretion leader. In this manner, amino acid residues that provide glycosylation sites may be substituted in a conservative manner for other amino acids in the secretion leader, such as with replacement of the codons for Gln to encode Asn.

The nucleotide sequences of the invention can be optimized for enhanced expression in the yeast host of interest. That is, these nucleotide sequences can be synthesized using yeast preferred condons for improved expression. See for example, U.S. Pat. Nos. 5,219,759 and 5,602,034.

Thus the nucleotide sequences for the promoter and termination regions and the nucleotide sequences encoding the PpSEC10 secretion leader and the mature Sec10p protein include the native forms as well as fragments and variants thereof. Likewise, the PpSEC10 secretion leader and the mature Sec10p protein include the native forms as well as fragments and variants thereof. The variant nucleotide sequences and variant polypeptides will be substantially homologous and functionally equivalent to the native nucleotide sequences and native polypeptides, respectively. A variant of a native nucleotide sequence or native polypeptide is "substantially homologous" to the native sequence or native polypeptide, respectively, when at least 70%, preferably at least 80%, more preferably about 90% to 95% or more, and most preferably when at least 98% of its nucleotide sequence for amino acid sequence, respectively, is identical to the native nucleotide sequence or native amino acid sequence. A variant may differ by as few as 1 to 10 amino acid residues, such as 6–10, as few as 5, as few as 4, 3, 2, or even 1 amino acid residue.

By "sequence identity" is intended the same nucleotides or amino acid residues are found within the variant sequence and a reference sequence when a specified, contiguous segment of the nucleotide sequence or amino acid sequence of the variant is aligned and compared to the nucleotide sequence or amino acid sequence of the reference sequence. Methods for sequence alignment and for determining identity between sequences are well known in the art. See, for example, Ausubel et al., eds. (1995) *Current Protocols in Molecular Biology*, Chapter 19 (Greene Publishing and Wiley-Interscience, New York); and the ALIGN program (Dayhoff (1978) in *Atlas of Protein Sequence and Structure*5:Suppl. 3 (National Biomedical Research Foundation, Washington, D.C.). With respect to optimal alignment of two nucleotide sequences, the contiguous segment of the variant nucleotide sequence may have additional nucleotides or deleted nucleotides with respect to the reference nucleotide sequence. Likewise, for purposes of optimal alignment of two amino acid sequences, the contiguous segment of the variant amino acid sequence may have additional amino acid residues or deleted amino acid residues with respect to the reference amino acid sequence. The contiguous segment used for comparison to the reference nucleotide sequence, or reference amino acid sequence will comprise at least 20 contiguous nucleotides, or amino acid residues, and may be 30, 40, 50, 100, or more nucleotides or. amino acid residues. Corrections for increased sequence identity associated with inclusion of gaps in the variant's nucleotide sequence or amino acid sequence can be made by assigning gap penalties.

When considering percentage of amino acid sequence identity, some amino acid residue positions may differ as a result of conservative amino acid substitutions, which do not affect properties of protein function. In these instances, percent sequence identity may be adjusted upwards to account for the similarity in conservatively substituted amino acids. Such adjustments are well known in the art. See, for example, Meyers & Miller (1988) *Computer Applic. Biol. Sci.* 4:11–17.

By "functionally equivalent" is intended that the variant nucleotide sequence defines a regulatory region or encodes an amino acid sequence for a polypeptide that has substantially the same function as the native regulatory region or native polypeptide. Hence, a variant of a nucleotide sequence for a PpSEC10 promoter will drive expression of an operably linked nucleotide sequence, while a variant of a nucleotide sequence for a PpSEC10 terminator will terminate expression of an operably linked nucleotide sequence. A variant of the nucleotide sequence encoding a PpSEC10 secretion leader will also encode a PpSEC10 secretion leader that directs movement of a mature protein sequence through the yeast'secretory pathway. Similarly, a variant of the nucleotide sequence encoding a Sec10p mature protein will also encode that mature protein. If the encoded PpSEC10 secretion leader or mature Sec10p protein is also a variant, it will possess substantially the same biological activity as the native PpSEC10 secretion leader or mature Sec10p protein, respectively. Functionally equivalent sequences of the present invention also encompass those fragments of the PpSEC10-derived regulatory nucleotide sequences, i.e., sequences for the promoter and terminator, and those fragments of the PpSEC10 secretion leader and Sec10p mature protein sequences, and variants thereof, that retain substantially the same function as the respective native sequence.

For example, a functionally equivalent fragment of a PpSEC10 promoter nucleotide sequence will drive expression of an operably linked nucleotide sequence. These fragments will comprise at least about 20 contiguous nucleotides, at least about 24 contiguous nucleotides, preferably at least about 50 contiguous nucleotides, more preferably at least about 75 contiguous nucleotides, even more preferably at least about 100 contiguous nucleotides, still more preferably at least about 200 contiguous nucleotides of the particular promoter nucleotide sequence disclosed herein. The nucleotides of such fragments will usually comprise the TATAA recognition sequence of the particular promoter sequence. Such fragments may be obtained by use of restriction enzymes to cleave the native PpSEC10 promoter nucleotide sequence disclosed herein; by synthesizing a nucleotide sequence from the native nucleotide sequence of the promoter; or may be obtained through the use of PCR technology. See particularly Mullis et al. (1987) *Methods Enzymol.* 155:335–350, and Erlich, ed. (1989) PCR *Technology* (Stockton Press, New York). Again, variants of these promoter fragments, such as those resulting from site-directed mutagenesis, are encompassed by the compositions of the present invention.

Methods are available in the art for determining functional equivalence. Promoter activity may be measured by Northern blot analysis. See, for example, Sambrook et al. (1989) *Molecular Cloning: A Laboratory Manual* (2d ed., Cold Spring Harbor Laboratory Press, Plainview, N.Y.), herein incorporated by reference. Biological activity can be measured using assays specifically designed for measuring activity of a native polypeptide. Additionally, antibodies raised against the biologically active native Sec10p protein can be tested for their ability to bind to the functionally equivalent variant, where effective binding is indicative of a protein having a conformation similar to that of the native protein.

The PpSEC10-derived regulatory and coding nucleotide sequences of the invention, and fragments and variants thereof, can be used as probes for the isolation of corresponding homologous sequences in other organisms, more particularly other yeasts. In this manner, methods such as PCR, hybridization, and the like can be used to identify such sequences having substantial sequence identity to the sequences of the invention. See, for example, Sambrook et al. (1989) *Molecular Cloning: A Laboratory Manual* (2d ed., Cold Spring Harbor Laboratory Press, Plainview, N.Y.) and Innis et al. (1990), *PCR Protocols: A Guide to Methods and Applications* (Academic Press, New York). Coding sequences isolated based on their sequence identity to the entire *Pichia pastoris* PpSEC10 gene regulatory and coding sequences set forth herein or to fragments and variants thereof are encompassed by the present invention.

In a PCR method, pairs of primers can be used in PCR reactions for amplification of DNA sequences from cDNA or genomic DNA extracted from any organism of interest. In addition, a single specific primer with a sequence corresponding to one of the nucleotide sequences disclosed herein can be paired with a primer having a sequence of the DNA vector in the cDNA or genomic libraries for PCR amplification of the sequences 5' or 3' to the nucleotide sequences disclosed herein. Similarly, nested primers may be used instead of a single specific primer for the purposes of the invention. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Ignis et al., eds. (1990) *PCR Protocols: A Guide to Methods and Applications* (Academic Press, New York).

In a hybridization method, all or part of a known nucleotide sequence can be used to screen cDNA or genomic libraries made from other organisms of interest. Methods for construction of such cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.). The so-called hybridization probes may be genomic DNA fragments, cDNA fragments, RNA fragments, or other oligonucleotides, and may be labeled with a detectable group such as $^{32}P$, or any other detectable marker. Probes for hybridization can be made by labeling synthetic oligonucleotides based on the known nucleotide sequence of interest. Degenerate primers designed on the basis of conserved nucleotides or amino acid residues in the known nucleotide or encoded amino acid sequence can additionally be used. Preparation of probes for hybridization is generally known in the art and is disclosed in Sambrook et al. (1989) *Molecular Cloning: A Laboratory Manual* (2d ed., Cold Spring Harbor Laboratory Press, Plainview, N.Y.), hereby incorporated by reference.

Using hybridization techniques, all or part of the specific known PpSEC10-derived regulatory or coding nucleotide sequence is used as a probe that selectively hybridizes to other possible PpSEC10 regulatory or coding nucleotide sequences present in a population of cloned genomic DNA fragments or cDNA fragments (i.e.,genomic or cDNA libraries) from a chosen organism. To achieve specific hybridization under a variety of conditions, such probes include sequences that a unique and are preferably at least about 20 nucleotides in length, and most preferably at least about 100 nucleotides in length. This technique may be used to isolate other possible PpSEC10 regulatory or coding nucleotide sequences from a desired organism or as a diagnostic assay to determine the presence of a PpSEC10 regulatory or coding nucleotide sequence in an organism. Hybridization techniques include hybridization screening of plated DNA libraries (either plaques or colonies; see, for example, Innis et al., eds. (1990) *PCR Protocols: A Guide to Methods and Applications* (Academic Press, New York)).

Thus, in addition to the native nucleotide sequences and fragments and variants thereof, the isolated nucleotide sequences of the invention also encompass homologous DNA sequences identified and isolated from other organisms by hybridization with entire or partial sequences obtained from the *Pichia pastoris* PpSEC10-derived regulatory and coding nucleotide sequences of the invention or variants thereof. Conditions that will permit other DNA sequences to hybridize to the DNA sequences disclosed herein can be determined in accordance with techniques generally known in the art. For example, hybridization of such sequences may be carried out under conditions of reduced stringency, medium stringency, or high stringency conditions (e.g., conditions represented by a wash stringency of 35–40% Formamide with 5×Denhardt's solution, 0.5% SDS, and 1×SSPE at 37° C.; conditions represented by a wash stringency of 40–45% Formamide with 5×Denhardt's solution, 0.5% SDS, and 1×SSPE at 42° C.; and conditions represented by a wash stringency of 50% Formamide with 5×Denhardt's solution, 0.5% SDS, and 1×SSPE at 42° C., respectively. See Sambrook et al. (1989) *Molecular Cloning: A Laboratory Manual* (2d ed., Cold Spring Harbor Laboratory Press, Plainview, New York). In general, sequences that, are substantially homologous and hybridize to the reference DNA sequences disclosed herein will have at least 70–75% sequence identity, 80–85% sequence identity, and even 90–95% sequence identity to the reference PpSEC10 sequences of the present invention.

The novel PpSEC10 regulatory and coding nucleotide sequences disclosed herein, and variants and fragments thereof, find use in methods directed to production of proteins, more particularly heterologous proteins, in a yeast host cell. The PpSEC10 nucleotide sequences individually or in various combinations may be provided in recombinant DNA constructs for introduction into a yeast host cell. By "recombinant" is intended genetic engineering of DNA fragments, which are assembled into the DNA construct of interest. These DNA constructs comprise all of the elements necessary for expression and secretion of a protein of interest from a yeast host cell. Thus, the DNA constructs of the invention, when introduced into a yeast host cell, can be expressed within that yeast host cell. Each DNA construct is provided with a plurality of restriction sites for insertion of the nucleotide coding sequence of interest that will be under the transcriptional regulation of the regulatory regions of the DNA construct. The DNA construct may additionally contain selectable marker genes, such as the *Pichia pastoris* histidinol dehydrogenase (HIS4) gene, to facilitate selection of stably transformed cells.

Such a recombinant DNA construct comprises in proper reading frame a nucleotide sequence for a yeast-recognized promoter, a nucleotide coding sequence for a yeast-derived secretion leader fused in frame to a nucleotide coding sequence for a desired protein of interest, and a nucleotide sequence for a yeast-recognized transcription terminator. By "in proper reading frame" is intended the individual nucleotide sequences are operably linked, and thus expression of the coding sequences is under the regulatory control of the yeast-recognized promoter and terminator sequences.

Expression of the coding sequences for the yeast secretion leader and the desired protein produces a hybrid precursor polypeptide, or so-called fusion protein. By "hybrid" precursor polypeptide is intended the coding sequence for the secretion leader is foreign to the coding sequence for the desired protein, and hence the two coding 'sequences are not natively expressed as a precursor polypeptide in the yeast host cell.

The hybrid precursor polypeptide comprises the necessary yeast-derived peptide sequences for movement of the desired protein sequence through the secretory pathway of the yeast host cell. Preferably the nucleotide sequence encoding the yeast secretion leader will terminate in a yeast-recognized processing site, such as a dibasic processing site such as Lys-Arg or Arg-Arg recognized in vivo by a Kex2 protease, such that the secretion leader is cleaved off of the secreted desired protein. One of skill in the art will recognize that the hybrid precursor polypeptide may contain an additional coding sequence for another protein of interest, such that the secreted protein itself is a fusion protein comprising two polypeptides joined by a peptide bond.

The distinguishing feature of the recombinant DNA constructs of the present invention is the inclusion, in proper reading frame,of at least one of the novel PpSEC10-derived nucleotide sequences disclosed herein. Thus, in addition to a nucleotide sequence encoding the protein of interest, a DNA construct of the present invention will further comprise a nucleotide sequence for the PpSEC10 promoter, a nucleotide sequence encoding the PpSEC10 secretion leader, and/or a nucleotide sequence for the PpSEC10 terminator, or a variant or fragment thereof.

By "yeast-recognized" promoter and terminator sequences is intended regulatory regions that; are functional in the yeast host cell. In one preferred embodiment of the invention, the recombinant DNA construct contains a PpSEC10 promoter disclosed herein, more particularly the PpSEC10 promoter having the sequence set forth in SEQ ID NO: 2 or a variant or fragment thereof.

Alternatively, when the recombinant DNA construct contains at least one other PpSEC10 nucleotide sequence, another type of yeast-recognized promoter may be used. This promoter may be a constitutive or inducible promoter, and may be native or analogous or foreign or heterologous to the specific yeast host. Additionally, the promoter may be the natural sequence or alternatively a synthetic sequence. By "foreign" is intended that the promoter is not found in the native yeast of interest into which the DNA construct comprising the promoter is introduced.

Other suitable native yeast promoters include, but are not limited to the wild-type a-factor promoter and promoters for the glycolytic enzymes phosphoglucoisomerase, phosphofructokinase, phosphotrioseisomerase, phosphoglucomutase, enolase, pyruvate kinase (PyK), glyceraldehyde-3-phosphate dehydrogenase (GAP or GAPDH), and alcohol dehydrogenase (ADH) (EPO Publication No. 284,044). See, for example, EPO Publication Nos. 120,551 and 164,556.

Synthetic hybrid promoters consisting of the upstream activator sequence of one yeast promoter, which allows for inducible expression, and the transcription activation region of another yeast promoter also serve as functional promoters in a yeast host. Examples of hybrid promoters include ADH/GAP, where the inducible region of the ADH promoter is combined with the activation region of the GAP promoter (U.S. Pat. Nos. 4,876,197 and 4,880,734). Other hybrid promoters using upstream activator sequences of either the ADH2, GAL4, GAL10, or PHO5 genes combined with the transcriptional activation region of a glycolytic enzyme such as GAP or PyK are available in the art (EPO Publication No. 164,556); herein incorporated by reference.

Yeast-recognized promoters also include naturally occurring non-yeast promoters that bind yeast RNA polymerase and initiate transcription of the coding sequence. Such promoters are available in the art. See, for example, Cohen et al. (1980) *Proc. Natl. Acad. Sci.* USA 77:1078; Mercereau-Puigalon et al. (1980) *Gene* 11:163: Panthier et al. (1980) *Curr. Genet.* 2:109); Henikoff et al. (1981) *Nature* 283:8;35; and Hollenberg et al. (1981) *Curr. Topics Microbiol. Immunol.* 96:119; herein incorporated by reference.

The terminator of the recombinant DNA construct may be native with the promoter, or may be derived from another source, providing that it is recognized by the yeast host. Thus in one preferred embodiment, the terminator is a PpSEC10 terminator, more particularly the PpSEC10 terminator having the sequence set forth in SEQ ID NO: 3 or a variant or fragment thereof. In this embodiment, the promoter may be the PpSEC10 promoter of the invention, or the promoter may be one of the other promoters identified above. Alternatively, when at least one other. PpSEC10 nucleotide sequence is present in the DNA construct, the terminator may be another yeast-recognized terminator, such as those for the α-factor protein (U.S. Pat. No. 4,870,008) and glycolytic enzymes mentioned above.

The DNA construct further comprises a nucleotide sequence encoding a yeast-derived secretion leader that serves to direct the polypeptide sequence for the protein of interest through the secretory pathway of the yeast host cell. Thus, in one preferred embodiment of the invention, this secretion leader is a PpSEC10 secretion leader, more particularly the PpSEC10 secretion leader set forth in SEQ ID NO: 4 or a variant or fragment thereof. Thus the DNA construct comprises a nucleotide sequence encoding this secretion leader, more particularly the nucleotide sequence set forth in SEQ ID NO: 5 or a sequence encoding a variant or fragment of the peptide sequence set forth in SEQ ID NO: 4. This particular DNA construct may further comprise a regulatory nucleotide sequence for a PpSEC10 promoter and/or terminator of the present invention.

Alternatively, if the DNA construct comprises at least one other PpSEC10 nucleotide sequence 6 of the invention, a yeast secretion leader derived from another yeast-secreted protein may be used to direct the polypeptide sequence for the protein of interest through the secretory pathway of the yeast host cell. Such a yeast-derived secretion leader may be a naturally occurring secretion leader comprising its native secretion signal, or the secretion leader may be a synthetic hybrid comprising a secretion signal derived from a different yeast-secreted protein. The yeast-secreted protein that serves as a source for the secretion leader may be foreign or native to the yeast host cell.

The secretion leader as defined herein comprises a functional secretion signal that is essential to bring about extracellular secretion of a protein from a yeast cell. In those instances where the secretion leader is a hybrid comprising a secretion signal other than the native signal, a number of secretion signals are well known in the art. Examples of secretion signals appropriate for the present invention include, but are not limited to, the secretion signal for α-factor (see, for example, U.S. Pat. No. 5,602,034; Brake et al. (1984) *Proc. Natl. Acad. Sci. USA* 81:4642:4646); invertase (WO 84/01153); PHO5 (DK 3614/83); YAP3 (yeast aspartic protease 3; PCT Publication No. 95/02059); and BAR1 (PCT Publication No. 87/02670). Alternatively, the secretion signal may be determined from genomic or cDNA libraries using hybridization probe techniques available in the art (see Sambrook et al. (1989) *Molecular Cloning: A Laboratory Manual* (2d ed., Cold Spring Harbor Laboratory Press, Plainview, N.Y.), or even synthetically derived (see, for example, WO 92/11378).

During entry into the ER, the secretion signal is cleaved off the precursor polypeptide at a processing site. The processing site can comprise any peptide sequence that is recognized in vivo by a yeast proteolytic enzyme. This processing site may be the naturally occurring processing site for the secretion signal. More preferably, the naturally occurring processing site will be modified, or the processing site will be synthetically derived, so as to be a preferred processing site. By "preferred processing site" is intended a processing site that is cleaved in vivo by a yeast proteolytic enzyme more efficiently than is the naturally occurring site. Examples of preferred processing sites include, but are not limited to, dibasic peptides, particularly any combination of the two basic residues Lys and Arg, that is Lys-Lys, Lys-Arg, Arg-Lys, or Arg-Arg, most preferably Lys-Arg. These sites are cleaved by the protease encoded by the KEX2 gene of *Saccharomyces cerevisiae* (see Fuller el al. *Microbiology* 1986:273–278) or the equivalent protease of other yeast species (see Julius et al. (1983) *Cell* 32:839–852). In the event that the Kex2 protease would cleave a site within the polypeptide sequence for the protein of interest, other preferred processing sites could be utilized such that the peptide sequence of interest remains intact (see, for example, Sambrook et al. (1989) *Molecular Cloning: A Laboratory Manual* (2d ed., Cold Spring Harbor Laboratory Press, Plainview, N.Y.).

For purposes of the present invention, the secretion leader preferably comprises its native secretion signal, as in the case of the PpSEC10 leader. The α-factor protein is another yeast-secreted protein that may serve as an alternative source of secretion leader comprising its native secretion signal. A number of genes encoding precursor α-factor proteins have been cloned and their secretion leader peptide sequences identified. See, for example, Singh et al. (1983) *Nucleic Acids Res.* 11:4049–4063; Kurjan et al., U.S. Pat. No. 4,546,082; U.S. Pat. No. 5,010,182; herein incorporated by reference. α-factor secretion leaders comprising their native secretion signals have been used to express heterologous proteins in yeast. See, for example, Elliott et al. (1983) *Proc. Natl. Acad. Sci. USA* 80:7080–7084;; Bitter et al. (1984) *Proc. Natl. Acad. Sci.* 81:5330–5334; Smith et al. (1985) *Science* 229:1219–1229; and U.S. Pat. Nos. 4,849, 407 and 5,219,759; herein incorporated by reference.

The recombinant DNA constructs comprising at least one PpSEC10 nucleotide sequence, of the invention may contain at least one additional nucleotide sequence of interest to be cotransformed into the yeast host. Alternatively, the additional nucleotide sequences of interest can be provided on a recombinant DNA construct other than the one comprising the PpSEC10 sequence. Where appropriate, the nucleotide sequence encoding the hybrid precursor polypeptide and any additional nucleotide sequences of interest may be optimized for increased expression in the transformed yeast, as previously noted.

Additional sequence modifications are known to enhance expression of nucleotide coding sequences in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the nucleotide coding sequence is modified to avoid predicted hairpin secondary mRNA structures.

In preparing the recombinant DNA construct, the various nucleotide sequence fragments may be manipulated so as to provide for the sequences in the proper orientation and, as appropriate, in the proper reading frame. Toward this end, adapters or linkers may be employed to join the nucleotide fragments or other manipulations may be involved to provide for convenient restriction sites, removal of superfluous nucleotides, removal of restriction sites, or the like. For this purpose, in vitro mutagenesis, primer repair, restriction, annealing, resubstitutions, e.g., transitions and transversions, may be involved. See particularly Sambrook et al. (1989) *Molecular Cloning: A Laboratory Manual* (2d ed., Cold Spring Harbor Laboratory Press, Plainview, N.Y.).

The recombinant DNA construct's restriction site for inserting the coding sequence for the protein of interest is a nucleotide sequence that is not present within the particular promoter or transcription terminator selected. The protein coding sequence may be inserted into the DNA construct using standard recombinant DNA methods. The protein may be identical to a naturally occurring protein or may contain modifications to alter its physicochemical properties, such as stability, activity, affinity for a particular ligand or receptor, antigenicity, therapeutic utility, or ability to be secreted from the host cell. Thus the nucleotide sequence encoding the mature protein of interest may a variant or fragment as previously defined above.

The protein of interest may be encoded by an endogenous gene in the yeast host cell or may be a protein not normally found in the host cell. It may be the precursor polypeptide form of the protein, and hence contain the native secretion signal and/or secretion leader, or it may be the mature form of the protein. In those instances where the protein is the precursor polypeptide form, modification of the native secretion leader to terminate in a yeast recognized processing site may facilitate secretion of the mature form of the protein of interest in a biologically active, properly folded conformation. See the copending application entitled "Method for Expression of Heterologous Proteins in Yeast," U.S. patent application Ser. No. 08/989,251, filed Dec. 12, 1997.

The protein of interest may also be a fusion protein consisting of two or more protein fragments fused together by means of peptide bond. In this manner, the first protein segment may comprise at least 6, 8, 10, 12, or 15 contiguous amino acids from the Sec10p amino acid sequence shown in SEQ ID NO: 6, or may comprise up to the full-length amino acid sequence for the mature Sec10p protein. Techniques for making fusion proteins, either recombinantly or by covalently linking two,o protein segments, are well known in the art. Thus the nucleotide sequence encoding the protein of interest may comprise a coding sequence for a Sec10p protein, more particularly the sequence set forth in SEQ ID NO: 7, in proper reading frame with a nucleotide sequence encoding the second protein segment. The second protein segment may be a full-length protein or a protein fragment. The second protein or protein fragment may be labeled with a detectable marker, such as an antibody tag, or may be an enzyme that will generate a detectable product. Enzymes suitable for this purpose, such as β-galactosidase, are well known in the art.

The protein of interest may be, for example, any protein of therapeutic or industrial use, including, but not limited to, a structural protein, an enzyme, a growth factor, a receptor for a ligand, an antibody, a hormone, a transport protein, a storage protein, a contractile protein, a cell differentiation factor, a repressor, a transcription factor, a cytokine, a haematopoietic factor, or a novel engineered protein. Illustrative proteins of interest include, but are not limited to, hormones and factors, such as insulin-like growth factor (IGF-I, IGF-II), platelet-derived growth factor (PDGF), growth hormone, somatomedins, epidermal growth factor (EGF), keratinocyte growth factor (KGF), fibroblast growth factor (FGF), nerve growth factor (NGF), TGF-beta, vascular endothelial cell growth factor (VEGF), luteinizing hormone, thyroid-stimulating hormone, epithelin precursor, epithelin 1, epithelin 2, oxytocin, insulin, vasopressin, renin, calcitonin, follicle-stimulating hormone, prolactin, erythropoietin (EPO), colony-stimulating factor (CSF), lymphokines such as interleukin-2, globins, immunoglobulins, interferons, enzymes, β-endorphin, enkephalin, dynorphin, etc.

In a preferred embodiment, the protein of interest is insulin-like growth factor I (IGF-I). IGF-I, a member of the somatomedin family, has 70 amino acid residues and a molecular mass of approximately 7.5 kDa. See Ringerknecht (1978) *J. Biol. Chem.* 253:2769 and *FEBS Lett.* 89:283. For a review of IGF-I, see Humbel (1990) *Eur J. Biochem.* 190:445–462. The nucleotide sequence encoding IGF-I that is assembled as part of the DNA construct may be genomic, cDNA, or synthetic DNA. The genes encoding the native forms of IGF-I have been sequenced, and several variants are well known in the art.

Suitable variants: can be IGF-I fragments, analogues, and derivatives. By "IGF-I fragment" is intended a protein consisting of only a part of the intact IGF-I sequence and structure, and can be a C-terminal deletion or N-terminal deletion of IGF-I. By "analogues" is intended analogues of either IGF-I or an IGF-I fragment that comprise a native IGF-I sequence and structure having one or more amino acid substitutions, insertions, or deletions. Peptides having one or more peptoids (peptide mimics) are also encompassed by the term analogue (see International Publication No. WO 91/04282). By "derivatives" is intended any suitable modification of IGF-I, IGF-I fragments, or their respective analogues, such as glycosylation, phosphorylation, or other addition of foreign moieties, so long as the IGF-I activity is retained. Methods for making IGF-I fragments, analogues, and derivatives are available in the art. See generally U.S. Pat. Nos. 4,738,921, 5,158,875, and 5,077,276; International Publication Nos. WO 85/00831, WO 92/04363, WO 87/01038, and WO 89/05822; and European Patent Nos. EP 135094, EP 123228, and EP 128733; herein incorporated by reference. GF-I variants will generally have at least 70%, preferably at least 80%, more referably about 90% to 95% or more, and most preferably about 98% or more amino acid sequence: identity to the amino acid sequence of the reference IGF-I molecule. A variant may differ by as few as 10, as few as 5, as few as 4, 3, 2, or even 1 amino acid residue.

The art provides substantial guidance regarding the preparation and use of such IGF-I variants, as discussed further below. A fragment of IGF-I will generally include at least 10 contiguous amino acid residues of the full-length molecule, preferably, 15 contiguous amino acid residues of the full-length molecule, and most preferably 25 or more contiguous amino acid residues of full-length IGF-I. In preparing the IGF-I variants, one of skill in the art can readily determine which modifications to the native protein nucleotide or amino acid sequence will result in a variant that retains the activity of the native IGF-I protein. These will generally be conservative amino acid substitutions that preserve the charge of the substituted residue (e.g., aspartic acid for glutamic acid).

Several IGF-I variants are known in the art and include those described in, for example, *Proc. Natl. Acad. Sci. USA* 83 (1986) 4904–4907; *Biochem. Biophys. Res. Commun.* 149 (1987) 398–404; *J. Biol. Chem.* 263 (1988) 6233–6239; *Biochem. Biophys. Res. Commun.* 165 (1989) 766–771; Forsbert et al. (1990) *Biochem. J.* 271:357–363; U.S. Pat. Nos. 4,876,242 and 5,077,276; and International Publication Nos. WO 87/01038 and WO 89/05822. Representative variants include one with a deletion of Glu-3 of the mature molecule, a variant with up to 5 amino acids truncated from the N-terminus, a variant with a truncation of the first 3 N-terminal amino acids (referred to as des(1–3)-IGF-I, des-IGF-I, tIGF-I, or brain IGF), and a variant including the first 17 amino acids of the B chain of human insulin in place of the first 16 amino acids of human IGF-I.

Nucleotide'sequences encoding IGF-I are known in the art. The IGF-I coding sequence may be chemically synthesized, such as with the phosphoramidite procedure as described by Urea (1983) *Proc. Natl. Acad. Sci. USA* 80:7461, and according to the Dayhoff amino acid sequences. The human gene for IGF-I has been chemically synthesized as disclosed in Niwa et al. (1986) *Annals New York Acad. Sci.* 469:31–52 or Buell et al. (1985) *Nucleic Acids Res.* 13:1923–1938; herein incorporated by reference. Nucleotide sequences encoding IGF-I may also be obtained by transcription of messenger RNA corresponding to IGF-I into its complementary DNA and converting the latter into double-stranded cDNA. Alternatively, the nucleotide sequence encoding IGF-I may be directly obtained from a known vector comprising an IGF-I gene by using restriction enzyme digestion to remove the gene for subsequent insertion into the recombinant DNA construct of the present invention. Such vectors are known in the art, as, for example, the vectors disclosed in Niwa et al. (1986) *Annals New York Acad. Sci.* 469:31–52 and Buell et al. (1985) *Nucleic Acids Res.* 13:1923–1938. See also International Publication No. WO 97/12044, herein incorporated by reference.

For any given protein of interest, the protein coding sequence is located in the construct adjacent to the nucleotide sequence encoding the PpSEC10 secretion leader. Transcription of the nucleotides encoding the secretion leader and protein coding sequence thus results in a fusion protein. After proteolytic processing, the mature protein is secreted into the culture medium. Preferably, two basic amino acids separate the two coding sequences, so that the secretion leader may be cleaved from the desired protein by a protease such as Kex2. The PpSEC10 secretion leader of the present invention (SEQ ID NO: 4 and variants or fragments thereof) terminates in this type of dibasic processing site.

The DNA construct of the present invention can be ligated into a replicon (e.g., plasmid, cosinid, virus, mini-chromosome), thus forming an expression vector that is capable of autonomous DNA replication in vivo. Such autonomously replicating vectors comprise yeast autonomous replication sequences and 2μ-based vectors. Preferably the replicon will be a plasmid. Such a plasmid expression vector will be maintained in one or more replication systems, preferably two replications systems, one that allows for stable maintenance within a yeast host cell for expression purposes, and one that provides for stable propagation within a prokaryotic host for cloning purposes. Examples of such yeast-bacteria shuttle vectors include Yep24 (Botstein et al. (1979) *Gene* 8:17–24; pC1/1 (Brake et al. (1984) *Proc. Natl. Acad. Sci. USA* 81:4642–4646), and Yrp17 (Stnichomb et al. (1982) *J. Mol. Biol.* 158:157). For cloning purposes, the plasmid vector comprising a recombinant DNA construct assembled with PpSEC10 nucleotide sequences of the present invention may be introduced into suitable host cells using a variety of techniques which are available in the art. These techniques include, but are not limited to, transferrin-polycation-mediated DNA transfer, transfection with naked or encapsulated nucleic acids, liposome mediated cellular fusion, intracellular transportation of DNA-coated latex beads, protoplast fusion, viral infection, electroporation, calcium phosphate-mediated transfection, and lithium salt-mediated transformation.

Additionally, a plasmid expression vector may be a high or low copy number plasmid, the copy number generally ranging from about 1 to about 200. With high copy number yeast vectors, there will generally be at least 10, preferably at least 20, and usually not exceeding about 250 copies in a single host. Either a high or low copy number vector may be desirable, depending upon the effect of the vector and of expression of the protein of interest on the host. See, for example, Brake et al. (1984) *Proc. Natl. Acad. Sci. USA* 81:4642–4646.

More preferably the recombinant DNA construct is ligated into a plasmid vector that allows for integration of the construct into the yeast genome. Examples of such integrating vectors are known in the art. See, for example, Botstein et al. (1979) *Gene* 8:17–24. Use of integrating vectors maximizes the stability of foreign protein production in a yeast host cell (Romanos et al. (1992) *Yeast* 8:423–488). Such a vector further comprises two segments of yeast host DNA sequences. For example, the DNA construct may be flanked with homologous regions of a yeast gene, such as the *Pichia pastoris* HIS4 gene, so that the construct can be integrated into the yeast genome by means of homologous recombination. The vector is linearized with a restriction enzyme, and the linearized DNA stimulates single crossover-type integration with the yeast host cell DNA.

Yeast host cells harboring multiple integrated copies of a recombinant DNA construct of the present invention may be generated by methods well known in the art. At least two such approaches have been developed. The first relies upon identifying multicopy strains that arise naturally as a low percentage of transformed cell populations. In this manner, large numbers of transformants are screened for production levels of the protein of interest by SDS-polyacrylamide gel electrophoresis, immunoblotting, or screened for multiple copies of the foreign gene using colony dot-blot hybridization. Alternatively, multiple copies of the recombinant DNA construct are constructed within a single vector prior to transformation of the yeast host cells. See, for example, Cregg et al. (1993) *Bio/Technology* 11:905–910, for a review of these methods. When a single vector is constructed with multiple copies of a DNA construct of the present invention, it may contain about 3 copies, preferably about 6 copies, more preferably about 8 copies of a particular DNA construct. It is within skill in the art to determine the optimal number of DNA constructs comprising the PpSEC10 nucleotide sequences and coding sequence for a given protein of interest and for a given strain of yeast.

The yeast cell to be transformed with an expression vector comprising at least one copy of a recombinant DNA construct that includes at least one PpSEC10 nucleotide sequence and a coding sequence for a protein of interest can be any yeast cell. By "yeast" is intended ascosporogenous yeasts (Endomycetales), basidiosporogenous yeasts, and yeast belonging to the Fungi Imperfecti (Blastomycetes). The ascosporogenous yeasts are divided into two families, Spermophthoraqceae and Saccharomycetaceae. The later is comprised of four subfamilies, Schizosaccharomycoideae (e.g., genus Schizosaccharomyces), Nadsonioideae, Lipomycoideae, and Saccharomycoideae (e.g., genera Pichia, Kluyveromyces, and Saccharomyces). The basidiosporogenous yeasts include the genera Leucosporidium, Rhodosporidium, Sporidiobolus, Filobasidium, and Filobasidiella. Yeast belonging to the Fungi Imperfecti are divided into two families, Sporobolomycetaceae (e.g., genera Sporobolomyces, Bullera) and Cryptococcaceae (e.g., genus Candida). Since the classification of yeast may change in the future, for the purposes of this invention, yeast shall be defined as described in Skinner et al., eds. 1980) *Biology and Activities of Yeast* (Soc. App. Bacteriol. Symp. Series No. 9). In addition to the foregoing, those of ordinary skill in the art are presumably familiar with the biology of yeast and the manipulation of yeast genetics. See, for example, Bacila et al., eds. (1978) *Biochemistry and Genetics of Yeast*; Rose and Harrison, eds. (1987) *The Yeasts* ($2^{nd}$ed.); Strathern et al; eds. (1981) *The Molecular Biology of the Yeast Saccharomyces*; herein incorporated by reference.

The selection of suitable yeast for the practice of the present invention is within the skill of the art. When selecting yeast hosts for expression, suitable hosts may include those shown to have, for example, good secretion capacity and low proteolytic activity. Yeast are generally available from a variety of sources, including the Yeast Genetic Stock Center, Department of Biophysics and Medical Physics, University of California, Berkeley, Calif.; and the American Type Culture Collection, Rockville, Md.

Of particular interest to the present invention are species within the genera Pichia, Kluyveromyces, Saccharomyces, Schizosaccharomyces, and Candida. Species of particular interest include *Pichia pastoris, Kluyveromyces lactis*, and the Saccharomyces species *S. cerevisiae, S. carlsbergensis, S. diastaticus, S. douglasii, S. kluyveri, S. norbensis*, and *S. oviformis*.

In one embodiment of the invention, the yeast host undergoing transformation to produce the protein of interest is a mutant *Pichia pastoris* strain that has a disabled PpSEC10 gene in its genome. By "disabled" is intended the wild-type gene has been genetically manipulated by man such that it does not express the wild-type PpSEC10 protein or expresses this protein at much reduced levels or in a form that is not capable of being secreted from the yeast cell. Absence of a secreted Sec10p protein or decreased production of this protein simplifies purification of a secreted protein of interest from the culture medium.

The mutant *Pichia pastoris* strain may be generated by a number of methods well known in the art. For example, the wild-type PpSEC10 gene sequence may be disabled by using site-directed mutagenesis methods so that the wild-type Sec10p protein is not transcribed, or if transcribed is not translated into a secretable Sec10p protein.

Alternatively, various portions of the PpSEC10 coding sequence can be deleted from the wild-type gene. It is within skill in the art to determine the size of deletion necessary to result in a disabled PpSEC10 gene. Thus, a disabled gene may result from deletion of a single nucleotide if such a deletion shifts the remaining coding sequence out of reading frame. Larger deletions can result in complete lack of expression of product. Alternatively, additional sequences can be inserted into the coding sequence to disrupt the reading frame of the gene of interest, causing a dramatically altered product to be expressed or resulting in the lack of expression of the product.

In one embodiment, a disabled gene may be prepared by inserting an auxotrophic marker gene into the PpSEC10 gene, thereby disrupting the PpSEC10 gene. Such auxotrophic marker genes can be selected from the Pichia or Saccharomyces HIS4 gene, the Pichia or Saccharomyces ARG4 genes, the Pichia or Saccharomyces URA3 genes, and the like.

In another embodiment of the invention, the PpSEC10 gene is disabled by replacement of the; wild-type PpSEC10 gene with a disabled PpSEC10 gene. Gene replacement is carried out, for example, by introducing the disabled PpSEC10 gene under transformation conditions suitable for the site-directed integration of the disabled gene into the genome of the yeast host at the specific locus of the wild-type PpSEC10 gene. Integration will replace or alter the host's endogenous gene. One means of introducing the disabled gene into the target PpSEC10 locus of a yeast host is to transform the yeast host with a linear DNA fragment comprising the disabled gene and having ends homologous to the 5' and 3' ends of the target wild-type PpSEC10 gene. This will direct, upon transformation, that homologous recombination occur at the specific locus of the PpSEC10 gene.

Those of skill in the art recognize that host Pichia strains for transformation with the above-described modified gene can be wild-type Pichia cells, which upon transformation with the disabled PpSEC10 gene, could be screened for reduced expression of the PpSEC10 gene product. The host strains employed can have one or more defects therein to assist in the identification and selection of desired transformants.

Thus, mutant strains comprising disabled PpSEC10 genes may be obtained, for example, as described above, by transformation with DNA constructs comprising a disabled PpSEC10 gene. Alternatively, a *Pichia pastoris* cell may be transformed with an expression vector comprising a DNA construct with an antisense nucleotide sequence for the native PpSEC10 gene. Provided with the PpSEC10 coding sequence disclosed herein, one skilled in the art can readily prepare such DNA constructs using standard recombinant DNA techniques.

Methods of introducing exogenous DNA into yeast hosts are well known in the art. There are a number of ways to transform yeast. For example, spheroplast transformation is taught by Hinnen et al. (1978) *Proc. Natl. Acad. Sci. USA* 75:1919–1933 and Stinchcomb et al., EPO Publication No. 45,573; herein incorporated by reference. Transformants are grown in an appropriate nutrient medium, and, where appropriate, maintained under selective pressure to insure retention of endogenous DNA. Where expression is inducible, growth can be permitted of the yeast host to yield a high density of cells, and then expression is induced.

Methods of culturing yeast cells in both small and large volume cultures are well known in the art. For example, the yeast *Pichia pastoris* may be cultured at cell densities greater than 100 g/liter dry weight. At least 0.3 g/l of a desired protein may be produced. Preferably, 0.5, 1.0, 2.5, 8.0, or 12 g/l of the desired protein is produced. Small-scale cultures of yeast cells comprising a recombinant DNA construct of the present invention may be screened for those cells that produce larger amounts of the protein of interest. Such screening is routine in the art. Components of the culture medium, such as the carbon or nitrogen sources, may be varied to increase the amount of desired protein secreted. When the PpSEC10 promoter :is used to regulate expression of a protein of interest, the carbon source in the medium may be, for example, glucose, glycerol, or methanol. Secretion of Sec10p protein is enhanced by the addition of casein amino acids to the medium. Preferably, the medium contains a 2×yeast nitrogen base.

The secreted protein of interest can be harvested by any conventional means and purified from media components by chromatography, electrophoresis, dialysis, solvent-solvent extraction, and the like. For example, the protein can be purified by diluting the cell-free medium with sodium acetate and contacting the diluted medium with a cation exchange resin, followed by hydrophobic interaction chromatography. Using this method, the desired protein is typically greater than 95% pure. Further purification may be undertaken using methods well known in the art.

A kit is provided for expressing a protein of interest in a yeast host cell. The kit provides a yeast cell and an expression vector comprising a recombinant DNA construct of the present invention. The yeast cell may be any of the yeast cells listed above; preferably, however, the yeast cell is a *Pichia pastoris* cell. The DNA construct comprises at least one of the PpSEC10 nucleotide sequences of the present invention in addition to the coding sequence for a mature protein of interest. When the vector is introduced into the yeast cell, the protein of interest is expressed.

The invention further provides a method of identifying a culture condition under which a desired protein can be expressed under the control of the PpSEC10 promoter. The method comprises culturing a *Pichia pastoris* cell and detecting Sec10p protein in the culture medium. A culture condition under which Sec10p protein is secreted into the medium is a condition under which a desired protein can be expressed under the control of the PpSEC10 promoter. Components of the medium that may be varied include the identity and/or concentration of salts, trace elements, carbon source, and amino acids. Biotin concentration may also be varied.

The novel Sec10p protein in the culture medium may be detected, for example, by radioimmunoassay, using radiolabeled Sec10p antibodies. A preparation of antibodies that specifically binds to Sec10p may be obtained using an amino acid sequence for the Sec10p protein of the present invention, more particularly the sequence set forth in SEQ ID NO:6 or any variant or fragment thereof. This Sec10p protein is encoded by a PpSEC10 nucleotide sequence, more particularly the nucleotide sequence set forth in SEQ ID NO:7 or a sequence encoding a variant or fragment of the polypeptide sequence set forth in SEQ ID NO:6. The antibodies may be polyclonal or monoclonal. Techniques for raising polyclonal and. monoclonal antibodies are well known in the art. The antibodies bind specifically to Sec10p epitopes, preferably epitopes not present on other *Pichia pastoris* proteins. Typically, a minimum number of contiguous amino acids to encode. an epitope is 6, 8, or 10. However, more may be used, for example, at least 15, 25, or 50, especially to form epitopes that involve noncontiguous residues. Specific binding antibodies do not detect other proteins on Western blots of *Pichia pastoris* proteins or in immunocytochemical assays or provide a signal at least ten-fold lower than the signal provided with Sec10p amino acids. Antibodies that bind specifically to Sec10p proteins include those that bind to the mature Sec10p protein, variants or fragments thereof, Sec10p degradation products, Sec10p fusion proteins, or to alternatively spliced forms of Sec10p protein. In a preferred embodiment of the invention the antibodies immunoprecipitate Sec10p protein solution and react with Sec10p protein on Western blots of polyacrylamide gels.

Techniques for purifying Sec10p antibodies are available in the art. In a preferred embodiment, antibodies are affinity purified by passing antiserum over a column to which a Sec10p protein, fusion protein, or polypeptide is bound. The bound antibody is then: eluted, for example using a buffer with a high salt concentration. Any such technique may be chosen to achieve the preparation of the invention. Anti-Sec10p antibodies may also be used to detect Sec10p protein in Western blots of polyacrylamide gels containing proteins from the culture medium.

The following examples are offered by way of illustration and not by way of limitation.

EXPERIMENTAL

Examples 1–4 demonstrate the cloning of the *Pichia pastoris* gene. Examples 5–7 demonstrate usefulness of the PpSEC10 promoter and secretion leader as components in an expression system. All *Pichia pastoris* expression constructs were generated in the standard Invitrogen (Sibia) plasmid.

Example 1

Isolation of the Novel PpSEC10 Protein

The protein composition of the medium from a stationary culture of *Pichia pastoris* was visualized using SDS-polyacrylamide gel electrophoresis. Samples of media from 72-hour (3 samples) and 96-hour (1 sample) cultures were reconstituted in 1×Tris-Tricine sample buffer and loaded onto a 10% Tricine gel. After elecitrophoresis, the gel was electroblotted to polyvinylidene fluoride transfer membrane (PVDF) and stained with Coomassie brilliant blue R250 (CBBR). Stained bands corresponding to 18 kDa were excised and loaded onto a sequencer for protein sequencing.

A major protein of approximately 18 kDa was observed and initially designated Sec18p. Subsequent sequence information revised the designation to Sec10p, as described below. The amino acid sequence for the isolated Sec10p protein is set forth in SEQ ID NO: 6. The nucleotide sequence encoding this amino acid sequence is set forth in SEQ ID NO: 7. Sequences were determined as described below in, Examples 2, 3, and 4.

Example 2

Determination of the N-terminal 35 Amino Acids of Mature Sec10p

Edmund degradation was used to determine the N-terminal 35 amino acids of the secreted mature Sec10p protein. The following sequence was determined: A-D-Y-M-C-H-M-A-C-G-L-A-I-Y-G-A-W-E-C-G-(P)-E-A-G-P-F-D-(S)-E-C-L-X-A-T-(D). This sequence corresponds to amino acids 1–35 of SEQ ID NO: 6.

Example 3

Cloning of DNA Encoding the N-terminal Amino Acids of Sec10p

Based on the amino acid sequence determined above, one 5' and two 3' degenerate PCR primers were designed. The 5' primer had the sequence 5'-GA(Y)TA(Y)ATGTG(Y)CA(Y) ATGGC-3' (SEQ ID NO: 10). The 3' primers had the following sequences: 5'-TC(N)GG(N)CC(R)CA(Y)TCCCA (N)GC-3' (SEQ ID NO: 11), and 5'-GC(Y)TC(N)GG(N)CC (R)CA(Y)TCCCA-3' (SEQ ID NO: 12), where Y=C or T; R=A or G; and N=G, A, T, orCfor all three degenerate primer sequences. Degenerate PCR was carried out with these primers using *Pichia pastoris* genomic DNA as a template. The degenerate PCR generated a 62 base-pair fragment.

The fragment was cloned into the vector pCRII (Invitrogen, San Diego, Calif.) and sequenced. The sequences of three independent clones were determined and the following consensus was reached: 5'-GATTATATGT GTCATATGGCTTGTGGTTTAGCCATCTACGGTGC CTGGGAATGCGGACCCGA-3' (SEQ ID NO: 13). The sequence of the degenerate product encoded an N-terminal portion of 20 amino acids.

Example 4

Cloning of the PpSEC10 Coding Sequence

The degenerate DNA sequence set forth in SEQ ID NO: 13 was used to design gene-specific primers in order to perform a rapid amplification of complementary ends (RACE) reaction. Two 5' and two 3' RACE primers were designed. The 5' primers were used in a 3' RACE reaction and the 3' primers were used in a 5' RACE reaction. Kits for running these reactions (Marathon, cDNA amplification kit) were purchased from Clontech (Palo Alto, Calif.). The 5' primers were: 5'-GCATTCCCAGGCACCGTAGATGGC-3' (SEQ ID NO: 14) and 5'-GCACCGTAGATGGCTAAAC CACAAGC-3' (SEQ ID NO: 15). The 3' primers were: 5'-GCCATCTACGGTGCCTGGGAATGC-3' (SEQ ID NO: 16) and 5'-GCTTGTGGTTTAGCCATCTACGGTGC-3' (SEQ ID NO: 17).

A cDNA library was generated from *Pichia pastoris* using standard techniques. The 3' and 5' RACE reactions were performed with all four gene specific primers and were designed to produce fragments whose sequences overlapped. Reactions performed with three of the primers resulted in PCR products of a reasonable size.

The RACE products were cloned and sequenced, and the Sec10p coding sequence set forth in SEQ ID NO: 7 was obtained. The amino acid sequence for translated mature Sec10p protein product of this sequence is set forth in SEQ ID NO: 6.

Five prime and 3' primers were then created to amplify the entire coding sequence for the PpSEC10 precursor polypeptide coding sequence using PCR. The 5' primer was 5'-ATGCTATTCAACAAATTTGCCGCAACCC-3' (SEQ ID NO: 18) and the 3' primer was 5'-TTAAACA CTAGTGGGTGTATAGGTTTGG-3' (SEQ ID NO: 19). PCR with these primers yielded the mature Sec10p coding region set forth in SEQ ID NO: 7, which has the translated amino acid sequence set forth in SEQ ID NO: 6. The PpSEC10 secretion leader has the sequence set forth in SEQ ID NO: 5. The translated amino acid sequence for this secretion leader sequence is set forth in SEQ ID NO: 4.

Example 5

Use of, the PpSEC10 Secretion Leader to Direct the Secretion of Acid Phosphatase and IGF-I from *Pichia pastoris*

Initial studies utilized the *Pichia pastoris* acid phosphatase (Pho1p) as a reporter protein. The PHO1 encoded acid phosphatase is normally secreted from *P. pastoris* (Payne et al. (1995) *Gene* 163:19–26) and is easily assayed. In this example, the secretion of acid phosphatase directed by the *Saccharomyces cerevisiae* α-factor (Mfα), *P. pastoris* PpSEC10, and *P. pastoris* PHO1 secretion leaders was compared. A DNA construct comprising the acid phosphatase gene, with either the α-factor, PpSEC10, or PHO1 secretion leader, operably linked to regulatory regions cloned into vector PpAO815 (Invitrogen, San Diego, Calif.) was used for transformation of a *P. pastoris* strain.

The total acid phosphatase activity secreted (absorbance at 420 nM) and the acid phosphatase activity secreted per optical density of the *P. pastoris* culture ($OD_{650}$) were determined. It is clear from Tables 1 and 2 that the PpSEC10 secretion leader performs at least as well as the *S. cerevisiae* α-factor secretion leader.

TABLE I

Acid Phosphatase activity per OD650, measured by absorbency at 420 nM.

|  | 24 hr | 48 hr | 72 hr | 96 hr |
| --- | --- | --- | --- | --- |
| Mfα | 0.927 | 1.74 | 2.34 | 1.550 |
| PpSEC10 | 0.763 | 1.91 | 2.63 | 1.810 |
| PHO1 | 2.300 | 3.45 | 2.84 | 0.706 |

The highest value for the negative control was 0.029.

TABLE 2

Total acid phosphatase activity, measured by absorbency at 420 nM.

|  | 24 hr | 48 hr | 72 hr | 96 hr |
| --- | --- | --- | --- | --- |
| Mfα | 2.17 | 5.44 | 8.70 | 6.15 |
| PpSEC10 | 1.82 | 6.39 | 10.60 | 7.77 |
| PHOA | 5.72 | 10.90 | 10.70 | 3.15 |

We also tested the PpSEC10 secretion leader's ability to direct the secretion of recombinant human IGF-I (rhIGF-I). All of the DNA constructs tested utilized the alcohol oxidase (AOX) promoter. The rhIGF-I gene used in this construct, and in constructs described in Example 7, was isolated from a yeast strain with an integrated vector. The coding sequence for this gene is described in International Publication No. WO 97/12044, herein incorporated by reference. Preliminary experiments with an ARS (autonomous replicating sequence) vector established that the PpSEC10 secretion leader could direct the secretion of rhIGF-I. In order to compare the PpSEC10 secretion leader with the present production strain, plasmids with increasing copies of rhIGF-I DNA constructs were isolated and integrated into the Pichia genome. The current rhIGF-I production strain (SMD1120) has 8 integrated copies of the rhIGF-l DNA construct and employs the α-factor secretion leader. Transformants with as many as 10 copies of a DNA construct containing the PpSEC10 secretion leader and rhIGF-I coding regions were tested. The best result was obtained from the strain containing 3 copies, which produced less than 20 percent as much as SMD1120 (data not shown).

Several approaches to improve IGF-I expression with the PpSEC10 secretion leader are possible. There is some indication from past work that the introduction of a glycosylation site(s) into the secretion leader facilitates the secretion of heterologous proteins that are themselves not glycosylated, as in the case for IGF-I. In addition, recent experiments with acid phosphatase secretion indicate that the PpSEC10 promoter may be significantly better than the alcohol oxidase promoter.

Example 6

PpSEC10 Secretory Leader Functions in *S. cerevisiae*

To determine the functionality of the *P. pastoris* PpSEC10 secretory leader in *S. cerevisiae*, the *P. pastoris* PHO1 was utilized as a reporter gene. The plasmids used in these experiments were 2μ-based and contained both the URA3 and d-LEU2 selectable marker genes (Barr et al. (1988) *J. Biol. Chem.* 263:16471–16478); (Brake et al. (1990) *Meth. Enzymol.* 185:408–421); (Cousens et al. (1987) *Gene* 61:265–275); (Payne et al. (1995) *Gene* 163:19–26).

The DNA construct inserted in these expression vectors contains the ADH/GAP hybrid promoter and the *S. cerevisiae* α-factor gene terminator as regulatory regions. In this example, the *P. pastoris* acid phosphatase gene, with either the *S. cerevisiae* α-factor or the *P. pastoris* PpSEC10 secretion leader was introduced into this DNA construct such that the reporter gene was operably linked to the regulatory regions.

*S. cerevisiae* strain AD4 was transformed with the expression vector and transformants selected on media lacking uracil. Single transformant colonies were suspended in water, then streaked onto plates with media lacking leucine (-leu). The growth in the absence of leucine enhances the plasmid copy number prior to growth in the expression medium. A colony from the -leu plate was used to inoculate a YEPD (8% glucose) overnight. The saturated overnight was diluted into a YEPD assay culture with 2% glucose to give an $OD_{650}$ of approximately 0.05. Samples were taken at 4 and 29 hours after inoculation and the media assayed for acid phosphatase activity. One hundred μl of culture was diluted into 0.7 ml 3 mM sodium acetate. Then 0.2 ml of substrate solution containing 5 mg/ml p-nitrophenylphosphate in 20 mM Tris pH 7.5 was added. The assay samples were incubated 60 minutes at 37° C. The reaction was stopped by the addition of 0.5 ml 1 M $Na_2CO_3$ and the absorbance at 420 nm ($A_{420}$) of the liberated p-nitrophenol was measured. The enzyme activity was calculated as micromoles of p-nitrophenol liberated per 15 minutes. The results from this experiment (Table 3) clearly demonstrate that the PpSEC10 secretion leader is as effective as the α-factor secretion leader for directing the secretion of acid phosphatase from *S. cerevisiae*.

TABLE 3

Comparison of Mfα and PpSEC11 secretion leaders for directing secretion of acid phosphatase from *S. cerevisiae*.

|  | $OD_{650}$ | Pho1p activity |
| --- | --- | --- |
| | 4 hours | |
| Untransformed Control | 0.03 | 0.26 |
| Mfα:PHO1 | 0.16 | 0.15 |
| Sec10:PHO1 | 0.01 | 0.19 |
| | 24 hours | |
| Untransformed Control | 14.05 | 0.38 |
| Mfα:PHO1 | 10.40 | 9.56 |
| Sec10:PHO1 | 10.40 | 10.50 |

Example 7

Secretion of Recombinant Human IGF-I (rhIGF-I) from *Pichia pastoris* Directed by the PpSEC10 Promoter and Signal Leader The DNA construct used in these experiments consisted of the coding sequences for the PpSEC10 secretion leader and rhIGF-I operably linked to the PpSEC10 promoter, and the PpSEC10 terminator sequence. This DNA construct was introduced into a plasmid that contains the *P. pastoris* HIS4 gene as a selectable marker. Several vectors were isolated with 1, 2, 3, 4, and 5 copies of the DNA construct. These vectors were used to transform the *P. pastoris* strain SMD1163. The transformants had the vector integrated into the genome.

Several colonies from each transformation as well as the untransformed SMD1163 were used to, inoculate 5 ml YEPD (2%) cultures. After 48 hours of growth at 30° C., these cultures were diluted 1 to 400 into 20 ml of SD media and growth was continued at 30° C. Samples were taken at 48 hours. Culture samples (0.60 ml) were centrifuged to remove cells and the cell free supernatant TCA precipitated. Two thirds of the TCA precipitate was analyzed by PAGE. The remaining one third was used for western analysis.

The results of these assays indicate that the transformants containing the PpSEC10 DNA construct expressed and secreted rhIGF-I (data not shown). The identity of the rhIGFiI band was confirmed by western analysis using anti-IGF-I antibodies. This observation establishes the efficacy of the PpSEC10 promoter, secretion leader, and terminator sequences to express and direct the secretion of a heterologous protein in *P. pastoris*.

Example 8

Construction of PpSEC10 Knockout Plasmid and Mutant *Pichia pastoris*

The following describes the construction of a plasmid that when digested with endonucleases generates a DNA fragment capable of recombining into the *Pichia pastoris* genome so as to render the PpSEC10 gene disabled. The ppGen2 clone (SEQ ID NO: 1) was digested with SstI and SpeI, which cut in the vector polylinker and the PpSEC10 promoter. This digest generated a 1661 base pair (bp) fragment that was cloned into a pLitmus28 vector (New England BioLabs Inc., Beverly, Mass.) digested with SstI and XbaI. In this cloning step, the SpeI overhang of the fragment clones into the XbaI site of the vector and neither site is regenerated. The resulting plasmid is named p3571.

Next, a second fragment was generated by digesting ppGen2 with BamHI and SpeI. This fragment contains the majority of the Sec10 gene but lacks the sequence encoding the initiation methionine and secretion signal. This fragment, which is 313 bp in length, was cloned into the BamHI- and SpeI-digested p357-1. The resulting plasmid is called p359-2.

Plasmid p359-2 was then BamHI digested and a 2 kb BamHI fragment containing the Kanamrycin resistance gene, ppKan, was cloned. The resulting plasmid is designated p367-4 and is the final construct. The ppKan fragment contains the Kan resistance marker from pUC4K (Invitrogen, San Diego, Calif.), which was engineered to use a *P. Pastoris* promoter and terminator. The promoter is from the URA3 gene, and the terminator is from the PEP4 gene.

The PpSEC10 gene was disabled by the single-step disruption method described by Stearns et al. (1990) *Meth. Enzymol.* 185:280–297. Plasmid p367-4 was digested with SpeI and SphI, which generates a 3.3 kb fragment containing over 1 kb of the PPSEC10 gene promoter and the entire ppKan and PpSEC10 gene segments. This 3.3 kb fragment was used to transform *P. pastoris* strains GST115 and SMD1163. Colonies that were resistant to G418 (geneticin)

were isolated (Scorer et al. (1994) *Bio/Technology* 12:181–184) and screened for their ability to produce Sec10p protein. Several SEC10-disabled derivatives of both strains were isolated.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A recombinant construct comprising in proper reading frame a nucleotide sequence for a promoter and a nucleotide sequence encoding a polypeptide, where said promoter drives transcription of an operably linked nucleotide sequence of interest, wherein said nucleotide sequence for said promoter is selected from the group consisting of:
   a) the nucleotide sequence set forth in SEQ ID NO: 2;
   b) a nucleotide sequence having at least 70% sequence identity to the nucleotide sequence set forth in SEQ ID NO: 2;
   c) a nucleotide sequence comprising at least 24 contiguous nucleotides of the sequence set forth in SEQ ID NO: 2; and
   d) a nucleotide sequence that hybridizes to any one of a), b), or c) under conditions of high stringency.

2. The construct of claim 1, wherein said nucleotide sequence for said promoter is the sequence set forth in SEQ ID NO: 2.

3. The construct of claim 1, wherein said polypeptide is selected from the group consisting of human IGF-I, a polypeptide having at least 70% sequence identity to said human IGF-I, and a fragment of said human IGF-I, wherein said fragment comprises at least 10 contiguous amino acid residues of an amino acid sequence for said human IGF-I.

4. The construct of claim 1, further comprising a nucleotide sequence encoding a functional: secretion leader, wherein said nucleotide sequence encoding said secretion leader is selected from the group consisting of:
   a) a nucleotide sequence encoding the amino acid sequence set forth in SEQ ID NO: 4;
   b) the nucleotide sequence set forth in SEQ ID NO: 5;
   c) a nucleotide sequence encoding an amino acid sequence having at least 70% sequence identity to the amino acid sequence set forth in SEQ ID NO: 4;
   d) a nucleotide sequence encoding at least 8 contiguous amino acid residues of the amino acid sequence set forth in SEQ ID NO: 4; and
   e) a nucleotide sequence that hybridizes to any of a), b), c), or d) under conditions of high stringency.

5. The construct of claim 4, wherein said nucleotide sequence for said promoter is the sequence set forth in SEQ ID NO: 2, and wherein said nucleotide sequence encoding said secretion leader is a nucleotide sequence encoding the amino acid sequence set forth in SEQ ID) NO: 4.

6. The construct of claim 1, further comprising a nucleotide sequence for a functional transcription terminator, wherein said nucleotide sequence for said terminator is selected from the group consisting of:
   a) the nucleotide sequence set forth in SEQ ID NO: 3;
   b) a nucleotide sequence having at least 70% sequence identity to the nucleotide sequence set forth in SEQ ID NO: 3;
   c) a nucleotide sequence comprising at least 24 contiguous nucleotides of the sequence set forth in SEQ ID NO: 3; and
   d) a nucleotide sequence that hybridizes to any one of a), b), or c) under conditions of high stringency.

7. The construct of claim 6, wherein said nucleotide sequence for said promoter is the sequence set forth in SEQ ID NO: 2, and wherein said nucleotide sequence for said terminator is the sequence set forth in SEQ ID NO: 3.

8. The construct of claim 4, further comprising a nucleotide sequence for a functional transcription terminator, wherein said nucleotide sequence for said terminator is selected from the group consisting of:
   a) the nucleotide sequence set forth in SEQ ID NO: 3;
   b) a nucleotide sequence having at least 70% sequence identity to the nucleotide sequence set forth in SEQ ID NO: 3;
   c) a nucleotide sequence comprising at least 24 contiguous nucleotides of the sequence set forth in SEQ ID NO: 3; and
   d) a nucleotide sequence that hybridizes to any one of a), b), or c) under conditions of high stringency.

9. The construct of claim 8, wherein said nucleotide sequence for said promoter is the sequence set forth in SEQ ID NO: 2, and wherein said nucleotide sequence encoding said secretion leader is a nucleotide sequence encoding the amino acid sequence set forth in SEQ ID NO: 4, and wherein said nucleotide sequence for said transcription terminator is the sequence set forth in SEQ ID NO: 3.

10. The construct of claim 8, wherein said polypeptide is selected from the group consisting of human IGF-I, a polypeptide having at least 70% sequence identity to said human IGF-I, and a fragment of said human IGF-I, wherein said fragment comprises at least 10 contiguous amino acid residues of an amino acid sequence for said human IGF-I.

11. A recombinant construct comprising in proper reading frame a nucleotide sequence for a yeast-recognized promoter, a nucleotide sequence encoding a functional secretion leader, and a nucleotide sequence encoding a polypeptide, wherein said nucleotide sequence encoding said secretion leader is selected from the group consisting of:
   a) a nucleotide sequence encoding the amino acid sequence set forth in SEQ ID NO: 4;
   b) the nucleotide sequence set forth in SEQ ID NO: 5;
   c) a nucleotide sequence encoding an amino acid sequence having at least 70% sequence identity to the amino acid sequence set forth in SEQ ID NO: 4;
   d) a nucleotide sequence encoding at least 8 contiguous amino acid residues of the amino acid sequence set forth in SEQ ID NO: 4; and
   e) a nucleotide sequence that hybridizes to any of a), b), c), or d) under conditions of high stringency.

12. The construct of claim 11, wherein said nucleotide sequence encoding said secretion leader is a nucleotide sequence encoding the amino acid sequence set forth in SEQ ID NO: 4.

13. The construct of claim 11, wherein said polypeptide is selected from the group consisting of human IGF-I, a polypeptide having at least 70% sequence identity to said human IGF-I, and a fragment of said human IGF-I, wherein said fragment comprises at least 10 continuous amino acids residues of an amino acid sequence for said human IGF-I, and wherein said nucleotide sequence encoding said secretion leader is a nucleotide sequence encoding the amino acid sequence set forth in SEQ ID NO: 4.

14. The construct of claim 11, further comprising a nucleotide sequence for a functional transcription terminator, wherein said nucleotide sequence for said terminator is selected from the group consisting of:
  a) the nucleotide sequence set forth in SEQ ID NO: 3;
  b) a nucleotide sequence having at least 70% sequence identity to the nucleotide sequence set forth in SEQ ID NO: 3;
  c) a nucleotide sequence comprising at least 24 contiguous nucleotides of the sequence set forth in SEQ ID NO: 3; and
  d) a nucleotide sequence that hybridizes to any one of a), b), or c) under conditions of high stringency.

15. The construct of claim 14, wherein said nucleotide sequence encoding said secretion leader is a nucleotide sequence encoding the amino acid sequence set forth in SEQ ID NO: 4, and wherein said nucleotide sequence for said transcription terminator is the sequence set forth in SEQ ID NO: 3.

16. A recombinant construct comprising in proper reading frame a nucleotide sequence for a yeast-recognized promoter, a nucleotide sequence encoding a polypeptide, and a nucleotide sequence for a functional transcription terminator, wherein said nucleotide sequence for said terminator is selected from the group consisting of:
  a) the nucleotide sequence set forth in SEQ ID NO: 3;
  b) a nucleotide sequence having at least 70% sequence identity to the nucleotide sequence set forth in SEQ ID NO: 3;
  c) a nucleotide sequence comprising at least 24 contiguous nucleotides of the sequence set forth in SEQ ID NO: 3; and
  d) a nucleotide sequence that hybridizes to any one of a), b), or c) under conditions of high stringency.

17. The construct of claim 16, wherein said nucleotide sequence for said terminator is the sequence set forth in SEQ ID NO: 3.

18. The construct of claim 16, wherein said polypeptide is selected from the group consisting of human IGF-I, a polypeptide having at least 70% sequence identity to said human IGF-I, and a fragment of said human IGF-I, wherein said fragment comprises at least 10 contiguous amino acids of an amino acid sequence for said human IGF-I.

19. A vector comprising at least one copy of the construct of claim 1.

20. The vector of claim 19, wherein said vector is an autonomously replicating vector.

21. The vector of claim 19, wherein said vector is an integrative vector.

22. A vector comprising at least one copy of the construct of claim 8.

23. A vector comprising at least one copy of the construct of claim 11.

24. A vector comprising at least one copy of the construct of claim 16.

25. A yeast host cell stably transformed with at least one copy of the construct of claim 1.

26. The yeast host cell of claim 25, wherein said yeast is selected from the group consisting of *Pichia pastoris, Saccharomyces cerevisiae*, and *Kluyveromyces lactis*.

27. A yeast host cell stably transformed with at least one copy of the construct of claim 8.

28. A yeast host cell stably transformed with at least one copy of the construct of claim 11.

29. The yeast host cell of claim 28, wherein said yeast host is *Pichia pastoris*, and wherein said polypeptide is selected from the group consisting of human IGF-I, a polypeptide having at least 70% sequence identity to said human IGF-I, and a fragment of said human IGF-I, wherein said fragment comprises at least 10 contiguous amino acid residues of an amino acid sequence for said human IGF-I, and wherein said nucleotide sequence encoding said secretion leader is a nucleotide, sequence encoding the amino acid sequence set forth in SEQ ID NO: 4.

30. A yeast host cell stably transformed with at least one copy of the construct of claim 16.

31. A mutant *Pichia pastoris* strain that has a disabled PpSEC10 gene.

32. The mutant *Pichia pastoris* strain of claim 31, wherein said strain is stably transformed with at least one copy of a construct comprising in proper reading frame a nucleotide sequence for a functional promoter and a nucleotide sequence encoding a polypeptide, wherein said nucleotide sequence for said promoter is selected from the group consisting of:
  a) the nucleotide sequence set forth in SEQ ID NO: 2;
  b) a nucleotide sequence having at least 70% sequence identity to the nucleotide sequence set forth in SEQ ID NO: 2;
  c) a nucleotide sequence comprising at least 24 contiguous nucleotides of the sequence set forth in SEQ ID NO: 2; and
  d) a nucleotide sequence that hybridizes to any one of a), b), or c) under conditions of high stringency.

33. The mutant *Pichia pastoris* strain of claim 31, wherein said strain is stably transformed with at least one copy of a construct comprising in proper reading frame a nucleotide sequence for a yeast-recognized promoter, a nucleotide sequence encoding a functional secretion leader, and:a nucleotide sequence encoding a polypeptide, wherein said nucleotide sequence encoding said secretion leader is selected from the group consisting of:
  a) a nucleotide sequence encoding the amino acid sequence set forth in SEQ ID NO: 4;
  b) the nucleotide sequence set forth in SEQ ID NO: 5;
  c) a nucleotide sequence encoding an amino acid sequence having at least 70% sequence identity to the amino acid sequence set forth in SEQ ID NO: 4;
  d) a nucleotide sequence encoding at least 8 contiguous amino acid residues of the amino acid sequence set forth in SEQ ID NO: 4; and
  e) a nucleotide sequence that hybridizes to any one of a), b), c), or d) under conditions of high stringency.

34. The mutant *Pichia pastoris* cell of claim 31, wherein said cell is stably transformed with at least one copy of a construct comprising in proper reading frame a yeast-recognized promoter, a nucleotide sequence encoding a polypeptide, and a nucleotide sequence for a functional transcription terminator, wherein said nucleotide sequence for said terminator is selected from the group consisting of:
  a) the nucleotide sequence set forth in SEQ ID NO: 3;
  b) a nucleotide sequence having at least 70% sequence identity to the nucleotide sequence set forth in SEQ ID NO: 3;

c) a nucleotide sequence comprising at least 24 contiguous nucleotides of the sequence set forth in SEQ ID NO: 3; and d) a nucleotide sequence that hybridizes to any one of a), b), or c) under conditions of high stringency.

35. A method for expression and secretion of a polypeptide using a yeast host cell as the expression system, said method comprising stably transforming said yeast host cell with a vector comprising at least one copy of a recombinant construct and culturing said transformed cell under conditions in which said construct is expressed, wherein said construct comprises in proper reading frame a nucleotide sequence for a functional promoter, a nucleotide sequence encoding a yeast-recognized secretion leader, and a nucleotide sequence encoding said polypeptide, wherein said nucleotide sequence for said promoter is selected from the group consisting of:

a) the nucleotide sequence set forth in SEQ ID NO: 2;

b) a nucleotide sequence having at least 70% sequence identity to the nucleotide sequence set forth in SEQ ID NO: 2;

c) a nucleotide sequence comprising at least 24 contiguous nucleotides of the sequence set forth in SEQ ID NO: 2; and d) a nucleotide sequence that hybridizes to any one of a), b), or c) under conditions of high stringency.

36. A method for expression and secretion of a polypeptide using a yeast host cell as the expression system, said method comprising stably transforming said yeast host cell with a vector comprising at least one copy of a recombinant construct and culturing said transformed cell under conditions in which said construct is expressed, wherein said construct comprises in proper reading frame a nucleotide sequence for a yeast-recognized promoter, a nucleotide sequence encoding a functional secretion leader, and a nucleotide sequence encoding said polypeptide, wherein said nucleotide sequence encoding said secretion leader is selected from the group consisting of:

a) a nucleotide sequence encoding the amino acid sequence set forth in SEQ ID NO: 4;

b) the nucleotide sequence set forth in SEQ ID NO: 5;

c) a nucleotide sequence encoding an amino acid sequence having at least 70% sequence identity to the amino acid sequence set forth in SEQ ID NO: 4;

d) a nucleotide sequence encoding at least 8 contiguous amino acid residues of the amino acid sequence set forth in SEQ ID NO: 4; and e) a nucleotide sequence that hybridizes to any one of a), b), c), or d) under conditions of high stringency.

37. A method for expression and secretion of a polypeptide using a yeast host cell as the expression system, said method comprising stably transforming said yeast host cell with a vector comprising at least one copy of a recombinant construct and culturing said transformed cell under conditions in which said construct is expressed, wherein said construct comprises in proper reading frame a nucleotide sequence for a yeast-recognized promoter, a nucleotide sequence encoding a yeast-recognized secretion leader, a nucleotide sequence encoding said polypeptide, and a nucleotide sequence for a functional transcription terminator, wherein said nucleotide sequence for said terminator is selected from the group consisting of:

a) the nucleotide sequence set forth in SEQ ID NO: 3;

b) a nucleotide sequence having at least 70% sequence identity to the nucleotide sequence set forth in SEQ ID NO: 3;

c) a nucleotide sequence comprising at least 24 contiguous nucleotides of the sequence set forth in SEQ ID NO: 3; and d) a nucleotide sequence that hybridizes to any one of a), b), or c) under conditions of high stringency.

38. An isolated polypeptide having an amino acid sequence selected from the group consisting of:

a) the amino acid sequence set forth in SEQ ID NO: 6;

b) an amino acid sequence comprising at least 8 contiguous amino acid residues of the amino acid sequence set forth in SEQ ID NO: 6; and c) an amino, acid sequence encoded by the nucleotide sequence set forth in SEQ ID NO: 7.

39. An antibody that selectively binds to the protein of claim 38.

40. A recombinant construct comprising in proper reading frame a promoter and a nucleotide sequence encoding a polypeptide, wherein said nucleotide sequence encoding said polypeptide is selected from the group consisting of:

a) a nucleotide sequence encoding the amino acid sequence set forth in SEQ ID NO: 6;

b) the nucleotide sequence set forth in SEQ ID NO: 7; and c) a nucleotide sequence encoding at least 8 contiguous amino acid residues of the amino acid sequence set forth in SEQ ID NO: 6.

41. A recombinant construct comprising in proper reading frame a nucleotide sequence for a promoter and a nucleotide sequence encoding a polypeptide, wherein said nucleotide sequence for said promoter is the nucleotide sequence set forth in SEQ ID NO: 2 or a nucleotide sequence having at least 95% sequence identity to the nucleotide sequence set forth in SEQ ID NO: 2, and wherein said polypeptide is human IGF-I.

42. The recombinant construct of claim 41, further comprising a nucleotide sequence encoding a secretion leader, wherein said nucleotide sequence encoding said secretion leader is a nucleotide sequence encoding the amino acid sequence set forth in SEQ ID NO: 4 or a nucleotide sequence encoding an amino acid sequence having at least 95% sequence identity to the amino acid sequence set forth in SEQ ID NO:4.

43. The recombinant construct of claim 42, wherein said nucleotide sequence encoding said secretion leader is the nucleotide sequence set forth in SEQ ID NO: 5.

44. A recombinant construct comprising in proper reading frame a nucleotide sequence for a yeast-recognized; promoter, a nucleotide sequence encoding a secretion leader, and a nucleotide sequence encoding a polypeptide, wherein said nucleotide sequence encoding said secretion leader is a nucleotide sequence encoding the amino acid sequence set forth in SEQ ID NO: 4 or a nucleotide sequence encoding an amino acid sequence having at least 95% sequence identity to the amino acid sequence set forth in SEQ ID NO:4, and wherein said polypeptide is human IGF-I.

45. The construct of claim 44, wherein said nucleotide sequence encoding said secretion leader is the nucleotide sequence set forth in SEQ ID NO: 5.

46. A method for expression and secretion of human IGF-I using a yeast host cell as the expression system, said method comprising stably transforming said yeast host cell with a vector comprising at least one copy of a recombinant construct and culturing said transformed cell under conditions in which said construct is expressed, wherein said construct comprises in proper reading frame a nucleotide sequence for a promoter, a nucleotide sequence encoding a yeast-recognized secretion leader, and a nucleotide sequence encoding said human IGF-I, wherein said nucleotide sequence for said promoter is the nucleotide sequence set forth in SEQ ID NO: 2 or a nucleotide sequence having at least 95% sequence identity to the nucleotide sequence set forth in SEQ ID NO:2.

47. The method of claim 46, wherein said nucleotide sequence encoding said yeast-recognized secretion leader is selected from the group consisting of:
   a) the nucleotide sequence set forth in SEQ ID NO: 5;
   b) a nucleotide sequence encoding the amino acid sequence set forth in SEQ ID NO: 4;
   c) a nucleotide sequence encoding a polypeptide that functions as a secretion leader and which has at least 70% sequence identity to the amino acid sequence set forth in SEQ ID NO: 4; and
   d) a nucleotide sequence that hybridizes to any one of a), b), or c) under conditions of high stringency, wherein said nucleotide sequence encodes a polypeptide that functions as a secretion leader.

48. The method of claim 46, wherein said nucleotide sequence encoding said yeast-recognized secretion leader is a nucleotide sequence encoding the amino acid sequence set forth in SEQ ID NO: 4 or a nucleotide sequence encoding an amino acid sequence having at least 95% sequence identity to the amino acid sequence set forth in SEQ ID NO: 4.

49. A method for expression and secretion of human IGF-I using a yeast host cell as the expression system, said method comprising stably transforming said yeast host cell with a vector comprising at least one copy of a recombinant construct and culturing said transformed cell under conditions in which said construct is expressed, wherein said construct comprises in proper reading frame a nucleotide sequence for a yeast-recognized promoter, a nucleotide sequence encoding a secretion leader, and a nucleotide sequence encoding said human IGF-I, wherein said nucleotide sequence encoding said secretion leader is a nucleotide sequence encoding the amino acid sequence set forth in SEQ ID NO: 4 or a nucleotide sequence encoding an amino acid sequence having at least 95% sequence identity to the amino acid sequence set forth in SEQ ID NO: 4.

50. The method of claim 49, wherein said nucleotide sequence encoding said secretion leader is the nucleotide sequence set forth in SEQ ID NO: 5.

51. The method of claim 49, wherein said sequence for said yeast-recognized promoter is the nucleotide sequence set forth in SEQ ID NO: 2 or a nucleotide sequence having at least 95% sequence identity to the nucleotide sequence set forth in SEQ ID NO: 2.

52. A recombinant construct comprising in proper reading frame a nucleotide sequence for a promoter, a nucleotide sequence encoding the secretion leader set forth in SEQ ID NO:4, and a nucleotide sequence encoding human IGF-I, wherein said nucleotide sequence for said promoter is the nucleotide sequence set forth in SEQ ID NO: 2.

53. The construct of claim 52, wherein said nucleotide sequence encoding said secretion leader is the nucleotide sequence set forth in SEQ ID NO: 5.

54. A yeast host cell stably transformed with at least one copy of the construct of claim 52.

55. A yeast host cell stably transformed with at least one copy of the construct of claim 53.

56. A method for expression and secretion of human IGF-I using a yeast host cell as the expression system, said method comprising stably transforming said yeast host cell with a vector comprising at least one copy of a recombinant construct and culturing said transformed cell under conditions in which said construct is expressed, wherein said construct comprises in proper reading frame a nucleotide sequence for a promoter, a nucleotide sequence encoding the secretion leader set forth in SEQ ID NO: 4, and a nucleotide sequence encoding human IGF-I, wherein said nucleotide sequence for said promoter is the nucleotide sequence set forth in SEQ ID NO: 2.

57. The method of claim 56, wherein said yeast host is selected from the group consisting of *Pichia pastoris, Saccharomyces cerevisiae*, and *Kluyveromyces lactis*.

58. The polypeptide of claim 38, wherein said amino acid sequence is the sequence set forth in SEQ ID NO: 6.

59. An isolated polypeptide comprising the amino acid sequence set forth in SEQ ID NO: 6.

60. A recombinant construct comprising in proper reading frame a promoter and a nucleotide sequence encoding a polypeptide comprising the amino acid sequence set forth in SEQ ID NO: 6.

61. The recombinant construct of claim 60, wherein said nucleotide sequence encoding said polypeptide comprises the nucleotide sequence set forth in SEQ ID NO: 7.

62. A recombinant construct comprising in proper reading frame a nucleotide sequence for a promoter and a nucleotide sequence encoding a polypeptide, wherein said nucleotide sequence for said promoter is the nucleotide sequence set forth in SEQ ID NO: 2.

63. A yeast host cell stably transformed with at least one copy of the construct of claim 62.

64. A recombinant construct comprising in proper reading frame a nucleotide sequence for a promoter, a nucleotide sequence encoding the secretion leader set forth in SEQ ID NO: 4, and a nucleotide sequence encoding a polypeptide.

65. The construct of claim 64, wherein said nucleotide sequence encoding said secretion leader is the nucleotide sequence set forth in SEQ ID NO: 5.

66. A yeast host cell stably transformed with at least one copy of the construct of claim 64.

67. A method for expression and secretion of a polypeptide using a yeast host cell as the expression system, said method comprising stably transforming said yeast host cell with a vector comprising at least one copy of a recombinant construct and culturing said transformed cell under conditions in which said construct is expressed, wherein said construct comprises in proper reading frame a nucleotide sequence for a yeast-recognized promoter, a nucleotide sequence encoding the secretion leader set forth in SEQ ID NO: 4, and a nucleotide sequence encoding said polypeptide.

68. The method of claim 67, wherein said yeast host is selected from the group consisting of *Pichia pastoris, Saccharomyces cerevisiae*, and *Kluyveromyces lactis*.

69. The method of claim 67, wherein said nucleotide sequence encoding said secretion leader is the nucleotide sequence set forth in SEQ ID NO: 5.

70. A method for expression and secretion of a polypeptide using a yeast host cell as the expression system, said method comprising stably transforming said yeast host cell with a vector comprising at least one copy of a recombinant construct and culturing said transformed cell under conditions in which said construct is expressed, wherein said construct comprises in proper reading frame a nucleotide sequence for a promoter, a nucleotide sequence encoding a yeast-derived secretion leader, and a nucleotide sequence encoding said polypeptide, wherein said nucleotide sequence for said promoter is the nucleotide sequence set forth in SEQ ID NO: 2.

71. The method of claim 70, wherein said yeast host is selected from the group consisting of *Pichia pastoris, Saccharomyces cerevisiae*, and *Kluyveromyces lactis*.

72. A method for expression of a polypeptide using a yeast host cell as the expression system, said method comprising stably transforming said yeast host cell with a vector comprising at least one copy of a recombinant construct and culturing said transformed cell under conditions in which said construct is expressed, wherein said construct comprises in proper reading frame a nucleotide sequence for a promoter and a nucleotide sequence encoding said polypeptide, wherein said nucleotide sequence for said promoter is the nucleotide sequence set forth in SEQ ID NO: 2.

73. The method of claim 72, wherein said yeast host is selected from the group. consisting of *Pichia pastoris, Saccharomyces cerevisiae*, and *Kluyveromyces lactis*.

* * * * *

UNITED STATES PATENT AND TRADEMARK OFFICE
CERTIFICATE OF CORRECTION

PATENT NO. : 6,410,264 B1
DATED : June 25, 2002
INVENTOR(S) : Crawford et al.

It is certified that error appears in the above-identified patent and that said Letters Patent is hereby corrected as shown below:

Column 22,
Line 38, after Table 2 insert: -- The highest value for the negative control was 0.064. --

Column 23,
Line 47, in the sub-heading in TABLE 3, "PpSECl 1" should read -- PpSEC10 --

Column 39,
Line 38, after "functional" cancel the colon "(:)";
Line 56, after the "ID" cancel the parenthesis.

Column 41,
Line 5, "Continuous amino acids" should read -- contiguous amino acid --;
Line 31, after "sequence" cancel the period "(.)".

Column 42,
Line 16, after "nucleotide" cancel the comma "(,)";
Line 41, "and:a" should read -- and a --.

Column 44,
Line 12, after "amino" cancel the comma "(,)";
Line 47, after "yeast-recognized" cancel the semicolon "(;)".

Signed and Sealed this

Twenty-eighth Day of January, 2003

JAMES E. ROGAN
*Director of the United States Patent and Trademark Office*

SEQUENCE LISTING

```
<160> NUMBER OF SEQ ID NOS: 19

<210> SEQ ID NO 1
<211> LENGTH: 5336
<212> TYPE: DNA
<213> ORGANISM: Artificial Sequence
<220> FEATURE:
<221> NAME/KEY: promoter
<222> LOCATION: (1180)..(2287)
<223> OTHER INFORMATION: PpSEC10 promoter
<220> FEATURE:
<221> NAME/KEY: sig_peptide
<222> LOCATION: (2288)..(2443)
<223> OTHER INFORMATION: PpSEC10 secretion leader
<220> FEATURE:
<221> NAME/KEY: mat_peptide
<222> LOCATION: (2444)..(2746)
<223> OTHER INFORMATION: Sec10p protein
<220> FEATURE:
<221> NAME/KEY: terminator
<222> LOCATION: (2747)..(3061)
<223> OTHER INFORMATION: PpSEC10 terminator
<220> FEATURE:
<221> NAME/KEY: TATA_signal
<222> LOCATION: (2214)..(2218)
<220> FEATURE:
<223> OTHER INFORMATION: Description of Artificial Sequence:Plasmid
      ppGen2 containing Pichia pastoris SEC10 gene

<400> SEQUENCE: 1
gaattcgagc tcggtacccg gggatctaaa caaaggacta cttatagaaa cctgctttgt        60
tgggtattaa atagttttgg taaacttaat cagccaatct ttgcacaagc acctgattgg      120
aagtatccgt ccgcttaagt tgaggcattg gctgtagaat gcgcaaattt agcatgtcat      180
ttccatccct gcttgattca gcatttccgg ttctgggatt acatctcaaa ggaacatcct      240
cttactgtag gtcacaacct tagtcttgca ttttttagaa aaaatgtat tgaacgaaca       300 tagtgtactc aaatgaacca tcttcgatat tataatatat tagtagttca aatcttcagt      360
ggtcctgttt gtcattcaaa tcagataacg gccttttgag cgccagtttt acaagaatag      420
aaacatcttt tgaatgtctg gttctcacat cctataaatc ctcgagcatt tgagtaccgt      480
agctctgctg aactagccga atttgaatta cataaggtta aaacttgccg ggtgaaaata      540
aagtaactag aatctcccca aaagtgacct cagctctgag agattataat tccagtgaat      600
aggctaggaa tgcctttatg catgttacga cacttgcatg ctccttgtgc cgcaacttat      660
gtccaagcaa ttagcaaaaa acattttca ggtacatgtg aaacaggttc agcaaggatg       720
ttcatgaaat ttgcaactag agatttatta taaggatggg agggacaacc caaataattg      780
acttcataag aacaatttgg gtgtagtcac tggtattccc tggtattcca tcagtccaac      840
agcttatcgg ctgaggatca attatcaaat aggggctgcc aatgactgat cccatatata      900
gagtgtggtg catacattat gaaagctcac taagaatgag atgatctgct gagagtcttc      960
gcaaccttaa tgtgtgtaat ttgagcactt ctggttatcg attagctatt gtggcgtccc     1020
```

-continued

```
cctttaaatt tatatataaa aaagcaaatc gaagccacat ataacccgtc aaattttgac    1080
atatagatac aggggaatat cctctgtata aacccaatc tggggttctt agattttcaa     1140
atacgggacg aaagaaatgt gagagtattg atatattctg tgatcttgg cttgatcgca     1200 gcaggttatt gacagttatg ccaggaactt agagcataaa actttgaact gttctgcaat    1260
atcagattgg accaaatact cactaccta attctcatat cttttcgata agaggttgct     1320
tcaattagtt ggctggccac aatctcaggt gctctgccat tatgaggtct gggtaagtcc    1380
agcttggaaa gcaatttcgc aaatcgcgat gtgtaaatct accccctccg atacaaatac    1440
aactttaggg gggtatcata ttagaatgca ttatacgagc caggggtaaa cctattcaga    1500
ggattcaagc cgaggatcaa ttcgcaacaa aagaattgac aatgctgtac aataatccgt    1560
agtaacctaa gactggttac atgtacgacc tcccgccccc cacgaccccc cacttataat    1620
ttcaaagttt cagggagcac aatatagagg ctttgtcaa gcagctgact agtaaaggta     1680
aagctatgga atatatgtga atggtgactt gacaccgatg cagaataccc actggaaagt    1740
cgggttttaa caggatagat gaactgtgat cctgtgcgac caaagcctag atattgtaag    1800
cacgagaatc tatatgactt gaaggttgta ttgctctgtg aacttaactt tcctgttctt    1860
caattttcaa atgttagctg cattttcatg atacggatag aagtcgttca atgacccgag    1920
ttatcaaagg gatagattga ttgcaattgg actcgtgcat gcacatttcg cttcgttacg    1980
gcacccgata cgaccacaag agtgtagtca agtgttatgg taggtggaaa tttcggattc    2040
atcgctaatc aacggggata gcgtattttt agtgaacttg acccttttt tccgaacaaa     2100 ataagccctc ccttcagcta aaagagggta gtgttgacat ttttaccatg caggggatg     2160 caaggagact gctgagcatg agttactgcc ttctaggttt tgacagaagt ttatataacg    2220
tgccattcat atcgttttaa cgtcagaact atctcctctt ctttgattct tcaacttaac    2280
actcaaaatg ctattcaaca aatttgccgc aaccctacta tctgctattg ctgcagtaaa    2340
tgcaatttct ttgccttcca ttgaacaggc acgtgaacat gtagccagag gtcttgttcc    2400
tcaggccttt gctgacgctt tggatcctgc tcttgaaaag agagctgatt acatgtgtca    2460
catggcttgt ggtttagcca tctacggtgc ctgggagtgt ggtcccgagg caggtccttt    2520
cgactcagaa tgtctatgtg ccactgattc ctccttttcg caacaaattg cagcttgtaa    2580
cgattgtgga tggtgtcttt accagtctta ctatggttac ctagctggtc ctttggacac    2640
ttgcggtttg ccaattactc caactggtac ccaatgtgct gagacagcta aacgttgac     2700 cccaactata ggtcctttcc aaacctatac acccactagt gtttaaatcc atcaaaacgg    2760
gtaggagttt gttaaactaa agttgtttct aggttcgtgt attttttag tagccagaat     2820 aaactctctt gcctttgtac acagaagaca aacgaaatca taattaaatc tcgctctcag    2880
aaaagaggga acctcatttc tggtagctaa atattgtaaa cttgagtaga acagaaaaat    2940
aaaaacatta ttgaactagt atggatgatt tagtatcaat gcaaagtatt gagaccctta    3000
caagcgatgg ttgtcatttt atttttttt tttttcttg agctgattgc acgtattgca     3060
gggagttctg catcttctgc aaaaaagctg ctggattaca tttgaaacaa tacaaattgg    3120
taccataaga aaatctgcat atacttcttt tcgtaccctt aaaggattag atttggactg    3180
ataagggttt gtagatagat atgttgcttt gtcttttctg gatgtaattc tacaacggaa    3240
tcaaaacttt caaagatatc ttcgcaaagt atcttcgcag tatctttgct gaggctaaag    3300
aaatagctgg ccattgcttc tgacttacta agtccacat tgaggaattt gaatatgcta     3360
actttgagga cagctgatca taggccatga aaagcagttg agagttttcc attcagtgga    3420
```

-continued

```
tacgaaactt acttctgtta caaaaaccat atcattatac ttatttcttt aaaaataact      3480
acatcatcaa gcaacagaac atgatccagc gaataagatt atttaactga atgtgggttt      3540
gcaaggatct cagatcctgg tattccattc tggtacaact gctcccactc ctcaacagtc      3600
ctctcttcgt tgcttggtga ccaattctca tattcctccc tggatccgac cggtcgctca      3660
gctattggag tgattctgaa gcagtgtctc acggagtcta ctggcaagaa atcgaaaaga      3720
gccgagtgga gcgctcttct gttatcccat gctaccacgg tgcctggttc atatgaagcc      3780
cttaattgta aatcaagtgc agttgcaatg tggttttcaa tgaattgcag tatcaaatca      3840 cttttcctctt gttttaaacc aataatccta gtcccgaacg ccttagcaaa tatagacttc      3900
ttgccgagaa ctgatggta tctgactagt ggatgaacat tttcagaggt gaactttttt       3960
cgttgaatgg aaccctagc taacgaatct tctgcctgtg ccttagcaga gtgaatcaat       4020
cttaggcctg acagaaagtt ctgaaaagta ggagacaacc tctcatatgc ctcgatggta      4080
tctgcaaaag ctgtatctcc cccactctcg gggccttcca aaattccaaa aaaagtagtt      4140
cccggaggtt gaagctcgta gtaacatca gagtgccaag tcatggccga acttttcttc       4200
tcaaaagaac gtgtcctgcc acttcgcttg taacttatat gaaactcagg atgtccttca      4260
ggggcaccag atgtttgatg gatatgtaaa ggcccaaaat gctgcccaaa cttttttaact     4320 tcagacaggc tcttgtcctt aagattttga tctctgaaga ccacaacacc tctctgggca     4380
acaaacaatg ccaagtcatc tttttgatca tttgatagtt cggataattg gatgccttcg      4440
acaacagaac caaactttgg agtaagtttc ttgatatcat gctttccgtt ctgcggaaag      4500
agtcttctaa gctctgggtc agcaaagaaa ccacgatcta cgtggttgaa tgccggttcg      4560
tcaacgaact tcagctcagg gttccaagtg gggagccatt gcggatacag tgaggcttct      4620
tttgcttccc tcgacacagt caacacacca tcagttctca cagaatcatt ctcaggaaag      4680
aagtgggtag gagagtctga tgttgtcttg tattcactgt tggcaattcc ttcgaacttt      4740
ttcttacggc cagcggctgt agcctcattt ggtttaaggg tgtagacggg atttactctt      4800
gccattgtgg attaagttga attatcaaaa atgttcgat atctatcaat aattctttct       4860
gagtttcagc catattttat attaaagaag gggtatgtgg taaatgtaag tttcaaatcc      4920
cttgtggatc cccacgataa atatcttcgc aatccatatc gtgtgattca atcacgtcac      4980
cttcttctcc tctacccgtc ggggcgcact cctaagccat agaaaacgtt ctcattttat      5040
ctcgatctga cgtaatccca actgagccaa gaagcaaaaa aatcatctgt caaaagtgtc     5100
agcaaaaagt gtacctcgct aattgggggg acgttggcaa tgaagttgcg ttagacattg      5160
tgtgcgccac accccacaac cacggcattc aaatgcctcg ctatcacatt attcattcta      5220
gttgttcgca agaatggtg ttctccaaac ttgacgtgct gtggctctca gggtccacat       5280
ctaacagtaa ttcaatctcc gaaatgcctt taaaactaca acgtctgctc ggatcc          5336
```

<210> SEQ ID NO 2
<211> LENGTH: 1108
<212> TYPE: DNA
<213> ORGANISM: Pichia pastoris
<220> FEATURE:
<223> OTHER INFORMATION: PpSEC10 promoter
<220> FEATURE:
<221> NAME/KEY: TATA_signal
<222> LOCATION: (1035)..(1039)

<400> SEQUENCE: 2

```
gtgatctttg gcttgatcgc agcaggttat tgacagttat gccaggaact tagagcataa        60
```

```
aactttgaac tgttctgcaa tatcagattg gaccaaatac tcactaccct aattctcata    120
tcttttcgat aagaggttgc ttcaattagt tggctggcca caatctcagg tgctctgcca    180
ttatgaggtc tgggtaagtc cagcttggaa agcaatttcg caaatcgcga tgtgtaaatc    240 tacccctcc gatacaaata caactttagg ggggtatcat attagaatgc attatacgag     300 ccagggtaa acctattcag aggattcaag ccgaggatca attcgcaaca aaagaattga     360
caatgctgta caataatccg tagtaaccta agactggtta catgtacgac ctcccgcccc    420
ccacgacccc ccacttataa tttcaaagtt tcagggagca caatatagag ggctttgtca    480
agcagctgac tagtaaaggt aaagctatgg aatatatgtg aatggtgact tgacaccgat    540
gcagaatacc cactggaaag tcgggtttta acaggataga tgaactgtga tcctgtgcga    600
ccaaagccta gatattgtaa gcacgagaat ctatatgact tgaaggttgt attgctctgt    660
gaacttaact ttcctgttct tcaattttca aatgttagct gcattttcat gatacggata    720
gaagtcgttc aatgacccga gttatcaaag ggatagattg attgcaattg gactcgtgca    780
tgcacatttc gcttcgttac ggcacccgat acgaccacaa gagtgtagtc aagtgttatg    840
gtaggtggaa atttcggatt catcgctaat caacggggat agcgtatttt tagtgaactt    900 gaccttttt ttccgaacaa aataagcccct cccttcagct aaaagagggt agtgttgaca    960
tttttaccat gcagggggat gcaaggagac tgctgagcat gagttactgc cttctaggtt   1020
ttgacagaag tttatataac gtgccattca tatcgtttta acgtcagaac tatctcctct   1080
tctttgattc ttcaacttaa cactcaaa                                       1108

<210> SEQ ID NO 3
<211> LENGTH: 315
<212> TYPE: DNA
<213> ORGANISM: Pichia pastoris
<220> FEATURE:
<223> OTHER INFORMATION: PpSEC10 terminator

<400> SEQUENCE: 3
atccatcaaa acgggtagga gtttgttaaa ctaaagttgt ttctaggttc gtgtattttt     60
ttagtagcca gaataaactc tcttgccttt gtacacagaa gacaaacgaa atcataatta    120
aatctcgctc tcagaaaaga gggaacctca tttctggtag ctaaatattg taaacttgag    180
tagaacagaa aaataaaaac attattgaac tagtatggat gatttagtat caatgcaaag    240
tattgagacc cttacaagcg atggttgtca tttattttt ttttttttt cttgagctga     300 ttgcacgtat tgcag                                                     315

<210> SEQ ID NO 4
<211> LENGTH: 52
<212> TYPE: PRT
<213> ORGANISM: Pichia pastoris
<220> FEATURE:
<223> OTHER INFORMATION: Amino acid sequence for the PpSEC10 secretion
      leader

<400> SEQUENCE: 4

Met Leu Phe Asn Lys Phe Ala Ala Thr Leu Leu Ser Ala Ile Ala Ala
 1               5                  10                  15

Val Asn Ala Ile Ser Leu Pro Ser Ile Glu Gln Ala Arg Glu His Val
                20                  25                  30

Ala Arg Gly Leu Val Pro Gln Ala Phe Ala Asp Ala Leu Asp Pro Ala
            35                  40                  45
```

Leu Glu Lys Arg
    50

<210> SEQ ID NO 5
<211> LENGTH: 156
<212> TYPE: DNA
<213> ORGANISM: Pichia pastoris
<220> FEATURE:
<223> OTHER INFORMATION: Nucleotide sequence for the PpSEC10 secretion
      leader

<400> SEQUENCE: 5
atgctattca caaatttgc cgcaaccct ctatctgcta ttgctgcagt aaatgcaatt      60
tctttgcctt ccattgaaca ggcacgtgaa catgtagcca gaggtcttgt tcctcaggcc    120
tttgctgacg ctttggatcc tgctcttgaa aagaga                             156

<210> SEQ ID NO 6
<211> LENGTH: 100
<212> TYPE: PRT
<213> ORGANISM: Pichia pastoris
<220> FEATURE:
<223> OTHER INFORMATION: Amino acid sequence for the Sec10p protein

<400> SEQUENCE: 6

Ala Asp Tyr Met Cys His Met Ala Cys Gly Leu Ala Ile Tyr Gly Ala
 1               5                  10                  15

Trp Glu Cys Gly Pro Glu Ala Gly Pro Phe Asp Ser Glu Cys Leu Cys
            20                  25                  30

Ala Thr Asp Ser Ser Phe Ser Gln Gln Ile Ala Ala Cys Asn Asp Cys
        35                  40                  45

Gly Trp Cys Leu Tyr Gln Ser Tyr Tyr Gly Tyr Leu Ala Gly Pro Leu
    50                  55                  60

Asp Thr Cys Gly Leu Pro Ile Thr Pro Thr Gly Thr Gln Cys Ala Glu
65                  70                  75                  80

Thr Ala Thr Thr Leu Thr Pro Thr Ile Gly Pro Phe Gln Thr Tyr Thr
                85                  90                  95

Pro Thr Ser Val
        100

<210> SEQ ID NO 7
<211> LENGTH: 303
<212> TYPE: DNA
<213> ORGANISM: Pichia pastoris
<220> FEATURE:
<223> OTHER INFORMATION: Nucleotide sequence for the Sec10p protein

<400> SEQUENCE: 7
gctgattaca tgtgtcacat ggcttgtggt ttagccatct acggtgcctg ggagtgtggt      60
cccgaggcag gtcctttcga ctcagaatgt ctatgtgcca ctgattcctc cttttcgcaa    120
caaattgcag cttgtaacga ttgtggatgg tgtctttacc agtcttacta tggttaccta    180
gctggtcctt tggacacttg cggtttgcca attactccaa ctggtaccca atgtgctgag    240
acagctacaa cgttgacccc aactataggt cctttccaaa cctatacacc cactagtgtt    300
taa                                                                 303

<210> SEQ ID NO 8
<211> LENGTH: 52
<212> TYPE: PRT
<213> ORGANISM: Pichia pastoris
<220> FEATURE:

<223> OTHER INFORMATION: Amino acid sequence for the PpSEC10 secretion
      leader variant

<400> SEQUENCE: 8

Met Leu Phe Asn Lys Phe Ala Ala Thr Leu Leu Ser Ala Ile Ala Ala
 1               5                  10                  15

Val Asn Asn Ile Ser Leu Pro Ser Ile Glu Gln Ala Arg Glu His Val
            20                  25                  30

Ala Arg Gly Leu Val Pro Gln Ala Phe Ala Asp Ala Leu Asp Pro Ala
        35                  40                  45

Leu Glu Lys Arg
    50

<210> SEQ ID NO 9
<211> LENGTH: 156
<212> TYPE: DNA
<213> ORGANISM: Pichia pastoris
<220> FEATURE:
<223> OTHER INFORMATION: Nucleotide sequence for the PpSEC10 secretion
      leader variant

<400> SEQUENCE: 9
atgctattca acaaatttgc cgcaaccta ctatctgcta ttgctgcagt aaataatatt     60
tctttgcctt ccattgaaca ggcacgtgaa catgtagcca gaggtcttgt tcctcaggcc    120
tttgctgacg ctttggatcc tgctcttgaa aagaga                             156

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:Degenerate
      5' PCR primer

<400> SEQUENCE: 10
gaytayatgt gycayatggc                                                20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:Degenerate
      3' PCR primer

<400> SEQUENCE: 11
tcnggnccrc aytcccangc                                                20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:Degenerate
      3' PCR primer

<400> SEQUENCE: 12
gcytcnggnc crcaytccca                                                20

<210> SEQ ID NO 13
<211> LENGTH: 62
<212> TYPE: DNA
<213> ORGANISM: Artificial Sequence
<220> FEATURE:

```
<223> OTHER INFORMATION: Description of Artificial Sequence:Consensus
      DNA sequence obtained by sequence comparison of three independent
      clones

<400> SEQUENCE: 13
gattatatgt gtcatatggc ttgtggttta gccatctacg gtgcctggga atgcggaccc      60
ga                                                                    62

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence:RACE 5'
      primer

<400> SEQUENCE: 14
gcattcccag gcaccgtaga tggc                                            24

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence:RACE 5'
      primer

<400> SEQUENCE: 15
gcaccgtaga tggctaaacc acaagc                                          26

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence:RACE 3'
      primer

<400> SEQUENCE: 16
gccatctacg gtgcctggga atgc                                            24

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence:RACE 3'
      primer

<400> SEQUENCE: 17
gcttgtggtt tagccatcta cggtgc                                          26

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence:5' primer
      used to isolate PpSEC10 coding sequence

<400> SEQUENCE: 18
atgctattca acaaatttgc cgcaaccc                                        28

<210> SEQ ID NO 19
<211> LENGTH: 28
<212> TYPE: DNA
```

-continued

```
<213> ORGANISM: Artificial Sequence
<220> FEATURE:
<223> OTHER INFORMATION: Description of Artificial Sequence:3' primer
      used to isolate PpSEC10 coding sequence

<400> SEQUENCE: 19
ttaaacacta gtgggtgtat aggtttgg                                            28
```